United States Patent
Watanabe

(10) Patent No.: US 11,413,012 B2
(45) Date of Patent: Aug. 16, 2022

(54) ULTRASOUND SIGNAL PROCESSING DEVICE AND ULTRASOUND SIGNAL PROCESSING METHOD

(71) Applicant: Konica Minolta, Inc., Tokyo (JP)

(72) Inventor: Yasuhito Watanabe, Takatsuki (JP)

(73) Assignee: KONICA MINOLTA, INC., Tokyo (JP)

(*) Notice: Subject to any disclaimer, the term of this patent is extended or adjusted under 35 U.S.C. 154(b) by 518 days.

(21) Appl. No.: 16/179,206

(22) Filed: Nov. 2, 2018

(65) Prior Publication Data

US 2019/0150888 A1 May 23, 2019

(30) Foreign Application Priority Data

Nov. 20, 2017 (JP) .............................. JP2017-223158

(51) Int. Cl.
| | |
|---|---|
| A61B 8/00 | (2006.01) |
| G01S 7/52 | (2006.01) |
| A61B 8/08 | (2006.01) |
| A61B 8/13 | (2006.01) |
| G01S 15/89 | (2006.01) |
| G10K 11/34 | (2006.01) |

(52) U.S. Cl.
CPC .......... *A61B 8/4272* (2013.01); *A61B 8/5207* (2013.01); *G01S 7/52028* (2013.01);
(Continued)

(58) Field of Classification Search
CPC ....... A61B 8/4272; A61B 8/5207; A61B 8/13; A61B 8/0858; G01S 15/8927;
(Continued)

(56) References Cited

U.S. PATENT DOCUMENTS

2015/0085617 A1* 3/2015 Savord ................ G01S 7/52095
367/138
2016/0120503 A1 5/2016 Tsushima
(Continued)

FOREIGN PATENT DOCUMENTS

| JP | 2005-052350 A | 3/2005 |
| JP | 2005052350 A * | 3/2005 |

(Continued)

OTHER PUBLICATIONS

"Ultrasound Diagnostic Equipment" by Masayasu Itou and Takashi Mochizuki, Corona Publishing Co., Ltd., Aug. 26, 2002, pp. 42-45 and partial English translation.
(Continued)

*Primary Examiner* — Jason M Ip
*Assistant Examiner* — Renee C Langhals
(74) *Attorney, Agent, or Firm* — Lucas & Mercanti, LLP

(57) ABSTRACT

An ultrasound signal processing device includes a transmitter that causes transducers to transmit an ultrasound beam, a receiver that, based on reflected waves received by reception transducers, generates reception signal sequences corresponding to the reception transducers, and a delay-and-sum section that, for a reference observation point in a region of interest, calculates delay times of reflected wave arrival to each of the reception transducers from the reference observation point as reference delay times and generates acoustic line signals by using the reference delay times corresponding to the reception transducers. For one or more dependent observation points in the region of interest that are contiguous in a depth direction from the reference observation point, the delay-and-sum section generates acoustic line signals by applying the reference delay times corresponding to the reception transducers.

19 Claims, 24 Drawing Sheets

(52) U.S. Cl.
CPC ...... *G01S 7/52046* (2013.01); *G01S 7/52085* (2013.01); *G01S 15/8927* (2013.01); *G10K 11/346* (2013.01); *A61B 8/0858* (2013.01); *A61B 8/13* (2013.01)

(58) Field of Classification Search
CPC ............. G01S 7/52085; G01S 7/52046; G01S 7/52028; G01S 7/52095; G10K 11/346
USPC ........................................................ 600/437
See application file for complete search history.

(56) References Cited

U.S. PATENT DOCUMENTS

2016/0278742 A1* 9/2016 Tsushima ............ G01S 7/52046
2017/0042510 A1* 2/2017 Ikeda ....................... A61B 8/14

FOREIGN PATENT DOCUMENTS

JP   2016-087453 A   5/2016
JP   2017-064249 A   4/2017

OTHER PUBLICATIONS

JPO, Notice of Reasons for Refusal for the corresponding Japanese application No. 2017-223158, dated Apr. 27, 2021, with English translation.

* cited by examiner

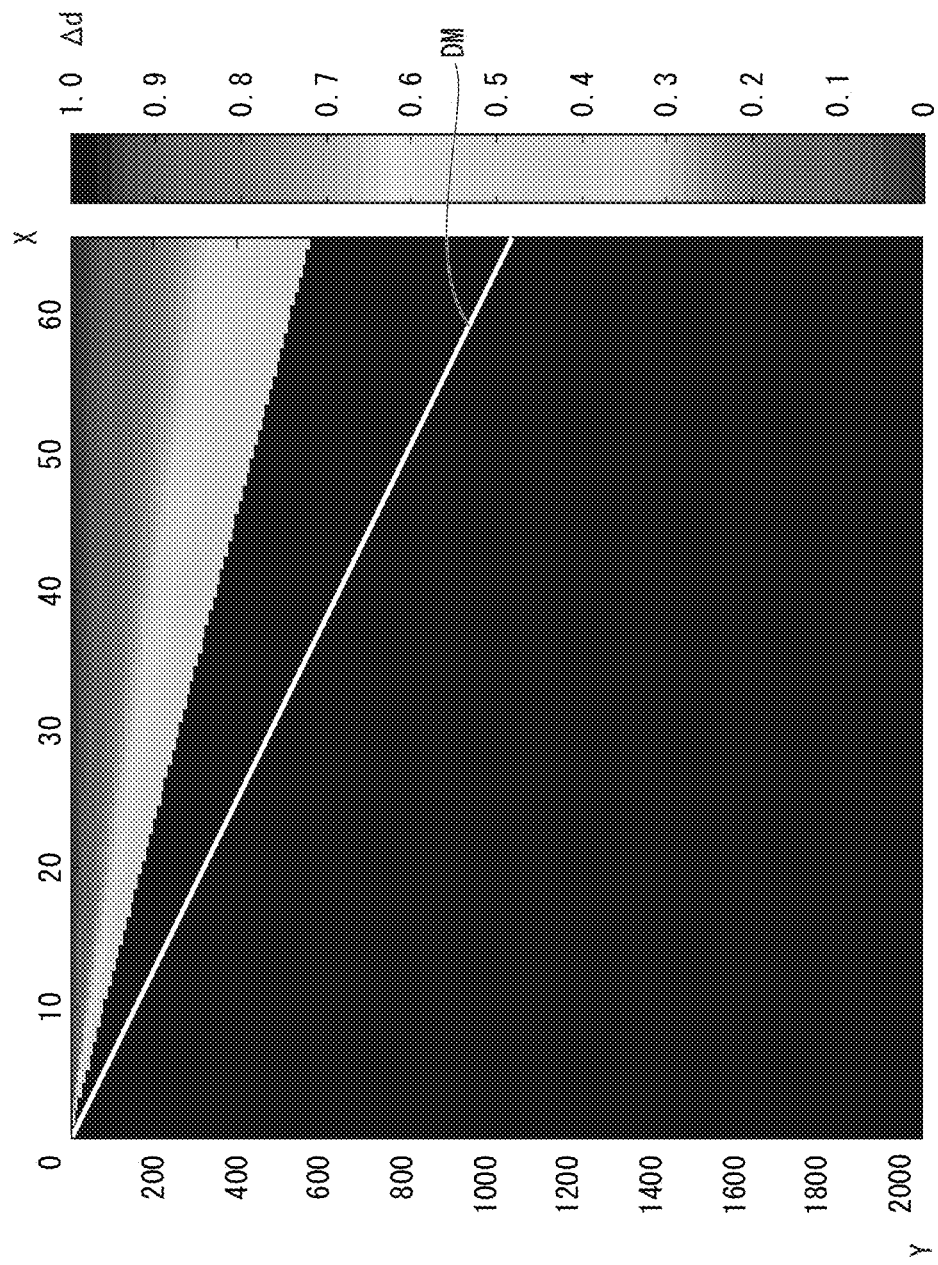

ULTRASOUND SIGNAL PROCESSING DEVICE AND ULTRASOUND SIGNAL PROCESSING METHOD

This application claims priority to Japanese Patent Application No. 2017-223158, filed Nov. 20, 2017, the contents of which are hereby incorporated by reference in their entirety.

BACKGROUND OF THE DISCLOSURE

Technical Field

The present disclosure relates to ultrasound signal processing devices and ultrasound signal processing methods, and in particular to reception beamforming processing methods in ultrasound diagnostic devices.

Description of the Related Art

An ultrasound diagnostic device transmits ultrasound to an inside of a subject via an ultrasound probe (hereinafter also referred to as a probe) and receives ultrasound reflected waves (echoes) caused by a difference in acoustic impedance of tissue in the subject. Further, based on an electric signal obtained from reception, an ultrasound diagnostic image illustrating structure of internal tissue of the subject is generated and displayed on a monitor (hereinafter also referred to as a display). Ultrasound diagnostic devices are widely used for morphological diagnoses of living bodies because they are not very invasive and can be used to observe the state of internal tissues in real time via tomographic images and the like.

For example, according to a conventional ultrasound diagnostic device described in "Ultrasound Diagnostic Devices" Corona Publishing Co., Ltd., Aug. 26, 2002, co-authored by Masayasu Ito and Tsuyoshi Mochizuki, a typical delay-and-sum method is described in pages 42 to 45 as a signal reception beamforming method based on received reflected ultrasound.

FIG. 23 is a schematic diagram illustrating a reception beamforming method of a conventional ultrasound diagnostic device. The conventional ultrasound diagnostic device includes a probe 201 that includes a plurality of ultrasound transducers 201a (hereinafter also referred to as transducers) that receive ultrasound reflected from inside a subject, and a reception beamformer 202 that electrically converts reflected ultrasound received by the transducers 201a to an electric signal and performs delay-and-sum processing on the electric signal. The reception beamformer 202 performs amplification, analogue to digital (A/D) conversion, and delay processing at a delay section 2021 for each of the transducers 201a on an electric signal based on reflected ultrasound obtained by the transducer 201a, then performs summing at a summing section 2022, outputting a result as an acoustic line signals. Delay amounts calculated by the delay section 2021 are calculated based on distances between a transducer located on a central axis of a transmission ultrasound beam and the transducers 201a. Specifically, when P is an arbitrary observation point located on the central axis of the transmission ultrasound beam in a subject, c is a transducer closest to the observation point P, dc is a distance between transducer c and observation point P, m is another transducer, dm is a distance between the observation point P and the transducer m, and Cs0 is a reference value of ultrasound acoustic velocity, ultrasound reflected from the observation point P reaches the transducer m with a delay of $(d/Cs0=dm/Cs0-dc/Cs0)$ from the time when the reflected wave reaches the transducer c from the observation point P (FIG. 24A). Calculate arrival time of a reflected wave from an observation point P at an arbitrary depth to a transducer c, and an arrival time of the reflected wave to a transducer m can be derived from an arrival time difference $(d/Cs0)$ between transducers. The delay section 2021 identifies reception signals at each transducer taking into account arrival time difference, and the summing section 2022 sums identified reception signals to generate an acoustic line signal (FIG. 24B).

SUMMARY

However, when increasing spatial resolution to achieve high resolution, the number of observation points included increases in proportion to the resolution, and therefore regarding delay-and-sum processing in view of transmission and reception delay, an amount of calculation increases. For this reason, hardware with high calculation processing capacity is required for high speed delay-and-sum calculation processing, which causes a problem of the cost of an ultrasound diagnostic device increasing. On the other hand, if the number of observation points is simply reduced, spatial resolution and signal to noise ratio may be insufficiently improved.

The present disclosure is made in view of these problems, and it is an object of the present disclosure to describe an ultrasound signal processing device capable of reducing a calculation amount in delay-and-sum processing while suppressing a decrease in spatial resolution and signal to noise ratio of an acoustic line signal, and an ultrasound diagnostic device using the ultrasound signal processing device.

To achieve at least one of the abovementioned objects, according to an aspect of the present disclosure, an ultrasound signal processing device reflecting one aspect of the present disclosure transmits an ultrasound beam into a subject by using an ultrasound probe in which transducers are arranged along an azimuth direction and generates acoustic line signals based on reflected waves obtained from the subject, the ultrasound signal processing device comprising: ultrasound signal processing circuitry, the ultrasound signal processing circuitry comprising: a transmitter that causes an array of transmission transducers selected from the transducers to transmit the ultrasound beam; a receiver that, based on reflected waves received by an array of reception transducers selected from the transducers, generates reception signal sequences corresponding to the reception transducers; and a delay-and-sum section that, for a reference observation point selected from observation points in a region of interest corresponding to an analysis target range of the subject, (i) calculates delay times of reflected wave arrival to each of the reception transducers from the reference observation point as reference delay times, and (ii) generates acoustic line signals by using the reference delay times corresponding to the reception transducers, and for one or more dependent observation points in the region of interest that are contiguous in a depth direction from the reference observation point, (iii) generates acoustic line signals by applying the reference delay times corresponding to the reception transducers.

BRIEF DESCRIPTION OF DRAWINGS

These and other objects, advantages, and features provided by one or more embodiments of the disclosure will become more fully understood from the detailed description given hereinbelow and the appended drawings which are given by way of illustration only, and thus are not intended as a definition of the limits of the present invention.

FIG. 10 is an enlargement of a range of depth direction coordinates of FIG. 9 from 0 to 2000, in which $\Delta d$ values equal to or greater than 0.5 are increased to 1.

FIG. 11A illustrates a difference in path length between a reception transducer Rwk and observation points P(0,j) and P(0,j+1) that are adjacent to each other in the depth direction, FIG. 11B illustrates a difference in path length between a reception transducer Rwk and observation points P(0,j) and P(0,j+4) that are 4 away from each other in the depth direction, and FIG. 11C illustrates a difference in path length between a reception transducer Rwk and observation points P(0,j) and P(0,j+8) that are 8 away from each other in the depth direction.

DETAILED DESCRIPTION

Hereinafter, one or more embodiments of the present disclosure will be described with reference to the drawings. However, the scope of the invention is not limited to the disclosed embodiments.

<Overall Configuration>

The following is a description of an ultrasound diagnostic device 100 pertaining to at least one embodiment, described with reference to the drawings.

Figure 1:
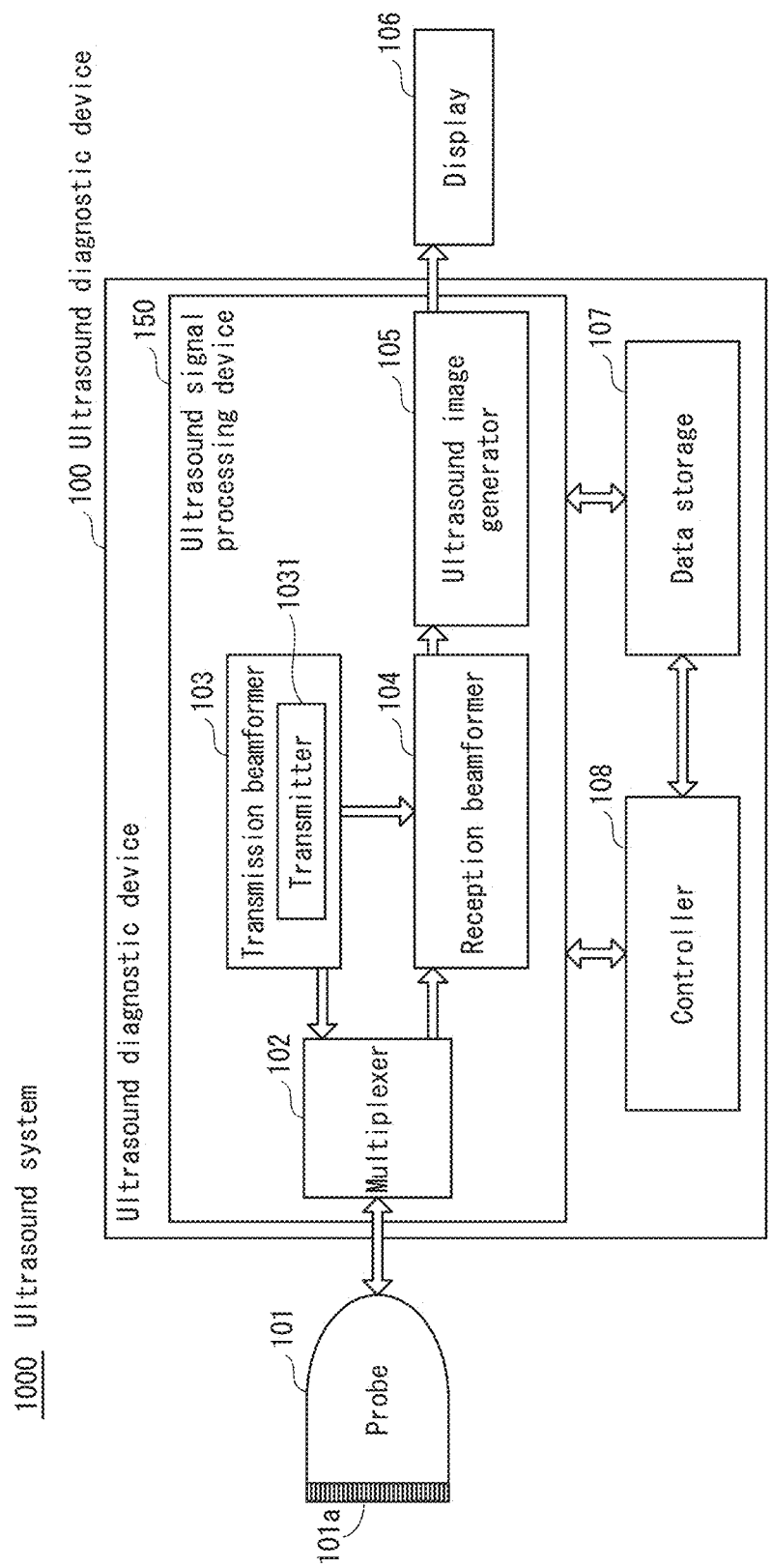
FIG. 1 is a function block diagram illustrating structure of an ultrasound diagnostic device 100 pertaining to an embodiment.

FIG. 1 is a function block diagram of an ultrasound diagnostic system 1000 pertaining to at least one embodiment. In FIG. 1, the ultrasound diagnostic system 1000 includes a probe 101 that has transducers 101a provided to an end surface of the probe 101 that transmit ultrasound towards a subject and receive reflected waves, the ultrasound diagnostic device 100 that causes the probe 101 to transmit and receive ultrasound and generates ultrasound images based on output signals from the probe 101, and a display 106 that displays an ultrasound image on a screen. The probe 101 and the display 106 are each connectable to the ultrasound diagnostic device 100. FIG. 1 illustrates the probe 101 and the display 106 connected to the ultrasound diagnostic device 100. The probe 101 and the display 106 may be incorporated in the ultrasound diagnostic device 100.

<Configuration of Ultrasound Diagnostic Device 100>

The ultrasound diagnostic device 100 includes a multiplexer 102 that selects transducers used for transmission or reception among the transducers 101a of the probe 101 and secures input/output of selected transducers, a transmission beamformer 103 that controls timing of high voltage application to the transducers 101a of the probe 101 in order to perform ultrasound transmission, and a reception beamformer 104 that amplifies and A/D converts electric signals obtained by the transducers 101a based on reflected ultrasound received by the probe 101, and performs reception beamforming to generate an acoustic line signal. Further, the ultrasound diagnostic device 100 includes an ultrasound image generator 105 that executes processing such as envelope detection and logarithmic compression with respect to acoustic line signals, which are output signals from the reception beamformer 104, in order to perform luminance conversion, in order to perform a coordinate transformation on the luminance signals to an orthogonal coordinate system, in order to generate an ultrasound image (B mode image), a data storage 107 that stores acoustic line signals output by the reception beamformer 104 and ultrasound images output by the ultrasound image generator 105, and a controller 108 that controls each component element of the ultrasound diagnostic device 100.

Of these, the multiplexer 102, the transmission beamformer 103, the reception beamformer 104, and the ultrasound image generator are included in the ultrasound signal processing device 150.

Elements of the ultrasound diagnostic device 100, for example the multiplexer 102, the transmission beamformer 103, the reception beamformer 104, ultrasound image generator 105, and the controller 108 are each implemented as a hardware circuit such as a field programmable gate array (FPGA), an application specific integrated circuit (ASIC), or the like. Alternatively, each element may be implemented by a programmable device such as a central processing unit (CPU), a general-purpose graphics processing unit (GPGPU), a processor, or the like, and software. These component elements can each be a single circuit component or an assembly of circuit components. Further, a plurality of component elements can be combined into a single circuit component or can be an aggregate of a plurality of circuit components.

The data storage 107 is a computer-readable storage medium, and may be a flexible disk, a hard disk, magneto-optical (MO), a digital versatile disc (DVD), digital versatile disc random access memory (DVD-RAM), semiconductor memory, or the like. Further, the data storage 107 may be a storage device that is external and connectable to the ultrasound diagnostic device 100.

The ultrasound diagnostic device 100 pertaining to the present embodiment is not limited to the ultrasound diagnostic device configuration illustrated in FIG. 1. For example, the ultrasound diagnostic device 100 may be configured without the multiplexer 102, and the probe 101 may incorporate the transmission beamformer 103 and/or the reception beamformer 104, or any portion thereof.

<Configuration of Elements of Ultrasound Diagnostic Device 100>

The ultrasound diagnostic device 100 pertaining to at least one embodiment is characterized by the reception beamformer 104 that generates an acoustic line signal for generating an ultrasound image by performing calculations related to an electric signal obtained from reception of reflected ultrasound by the probe 101. Thus, the present description largely focuses on description of structure and function of the reception beamformer 104 and the transmission beamformer 103 that causes ultrasound transmission from the transducers 101a of the probe 101. Structure other than that of the transmission beamformer 103 and the reception beamformer 104 may be the same as that used in publicly known ultrasound diagnostic devices, and it is possible to replace a beamformer of a publicly known ultrasound diagnostic device with a beamformer pertaining to the present embodiment.

The following is a description of structure of the transmission beamformer 103 and the reception beamformer 104.

1. Transmission Beamformer 103

The transmission beamformer 103 is connected to the probe 101 via the multiplexer 102 and controls timing of high voltage application to each of a plurality of transducers included in a transmission aperture Tx consisting of a transmission transducer array of all or a plurality of the transducers 101a of the probe 101 for transmitting ultrasound from the probe 101. The transmission beamformer 103 includes a transmitter 1031.

Based on a transmission control signal from the controller 108, the transmitter 1031 performs transmission processing to supply a pulsed transmission signal for causing transducers included in the transmission aperture Tx among the transducers 101a of the probe 101 to transmit an ultrasound beam. In transmission processing, a delay time is set for ultrasound beam transmission timing for each transducer, delaying ultrasound beam transmission by the delay time in order to focus an ultrasound beam.

The transmitter 1031 repeats ultrasound transmission while gradually shifting the transmission aperture Tx in an array direction for each ultrasound transmission, performing ultrasound transmission from all of the transducers 101a of the probe 101. Information indicating position of transducers included in the transmission aperture Tx is outputted to the data storage 107 via the controller 108. For example, when a total number of the transducers 101a of the probe 101 is 192, a number of transducers in the transmission aperture Tx may be selected from 20 to 100, for example, and gradually shifted per ultrasound transmission performed. Hereinafter, ultrasound transmission performed from the same transmission aperture Tx by the transmitter 1031 is also referred to as a "transmission event".

Figure 2:
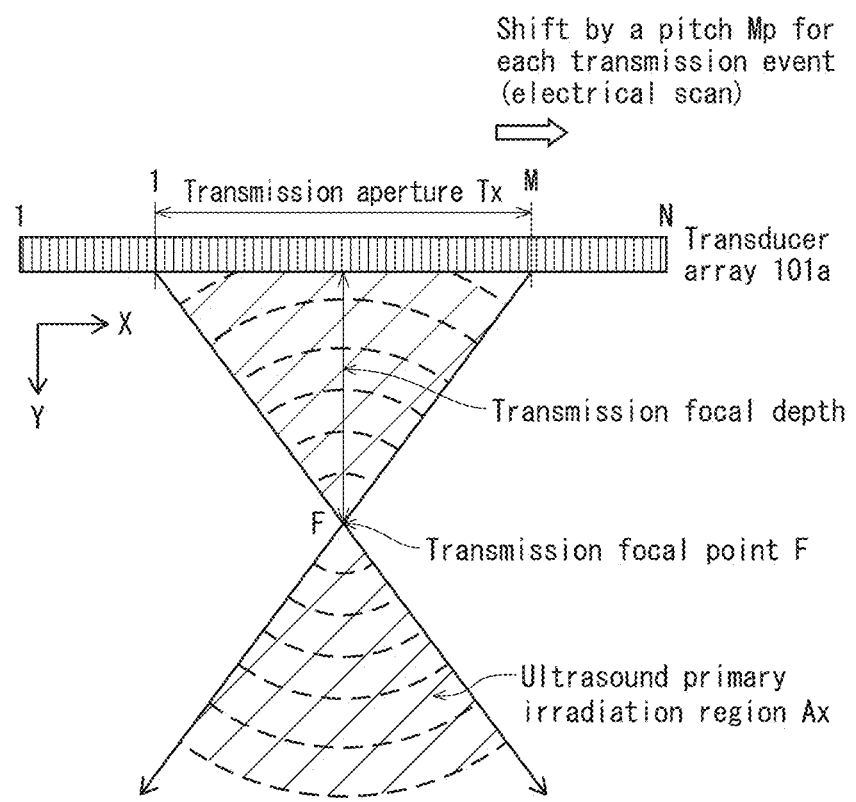
FIG. 2 is a schematic diagram illustrating a propagation path of an ultrasound transmission according to a transmission beamformer 103.

FIG. 2 is a schematic diagram illustrating a propagation path of an ultrasound transmission according to a transmission beamformer 103. In a given transmission event, an array of the transducers 101a contributing to ultrasound transmission are illustrated in FIG. 2. As illustrated in FIG. 2 and in the present description, the array direction (azimuth direction) of the transducers 101a is an X direction, and a depth direction in a subject normal to the azimuth direction is a Y direction.

By controlling transmission timing of each transducer so that transmission timing is delayed more the nearer a transducer is to a center of the transmission aperture Tx, the transmission beamformer 103 makes a wavefront of an ultrasound transmission transmitted from a transducer array in the transmission aperture Tx converge at a transmission focal point F at a certain depth in the subject. A focal depth of a transmission focal point F can be set arbitrarily. A wavefront converging at the transmission focal point F diffuses again and the ultrasound transmission propagates in an hourglass-shaped space delimited by two straight lines intersecting at the transmission focal point F with the transmission aperture Tx as the base. The hourglass-shaped region (indicated by hatching with diagonal lines) is referred to as an ultrasound primary irradiation region Ax.

2. Reception Beamformer 104

Figure 3:
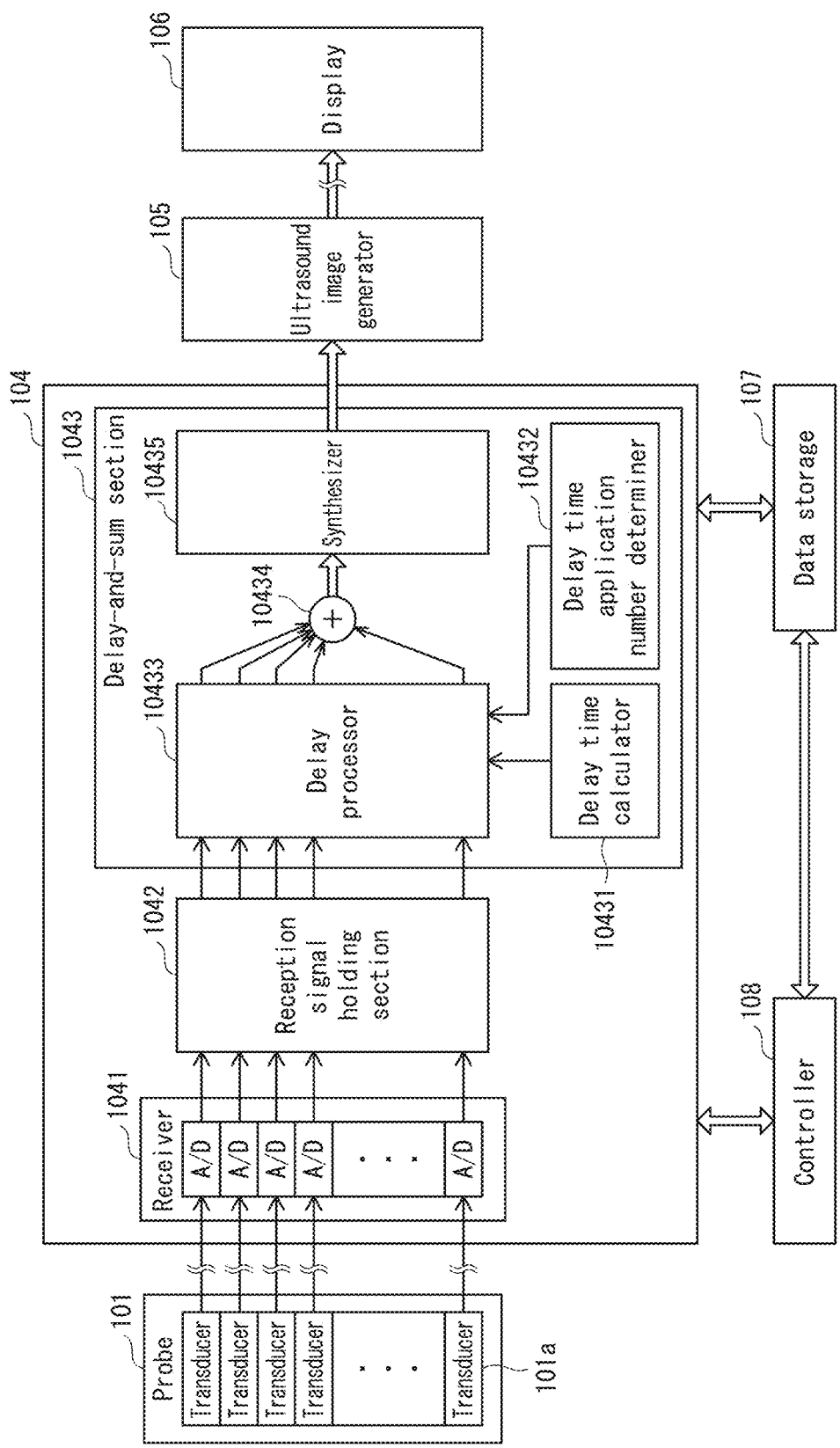
FIG. 3 is a function block diagram illustrating structure of a reception beamformer 104 of the ultrasound diagnostic device 100.

The reception beamformer 104 generates an acoustic line signal from an electrical signal obtained by a plurality of the transducers 101a based on reflected ultrasound received by the probe 101. An "acoustic line signal" is a reception signal with respect to an observation point after delay-and-sum processing is performed. Delay-and-sum processing is described in more detail later. FIG. 3 is a function block diagram illustrating structure of the reception beamformer 104. In FIG. 3, the reception beamformer 104 includes a receiver 1041, a reception signal holding section 1042, and a delay-and-sum section 1043.

The following describes structure of each element of the reception beamformer 104.

(1) Receiver 1041

The receiver 1041 is connected to the multiplexer 102 via the probe 101, and is a circuit that generates an analog-to-digital (AD) converted reception signal (radio frequency (RF) signal) after amplifying an electrical signal obtained by reception of reflected ultrasound by the probe 101 in correspondence with a transmission event. Reception signals are generated in a time sequence in transmission event order and outputted to the reception signal holding section 1042, which holds the reception signals.

Here, a reception signal (RF signal) is a digital signal obtained through AD conversion of an electrical signal converted from reflected ultrasound received by transducers, and forms a signal sequence in a direction of transmission (depth direction of subject) of ultrasound received by the transducers.

Figure 4:
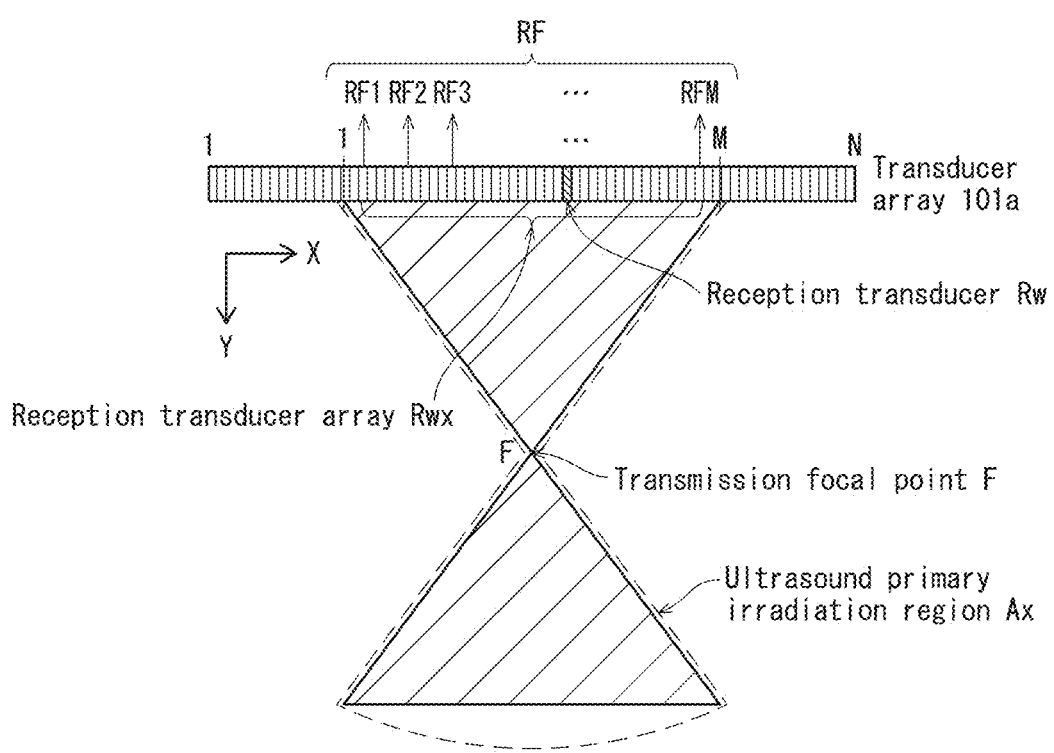
FIG. 4 is a schematic diagram for describing generation of a radio frequency signal sequence based on ultrasound reflected from an ultrasound primary irradiation region Ax.

FIG. 4 is a schematic diagram for describing generation of an RF signal sequence based on ultrasound reflected from the ultrasound primary irradiation region Ax. The receiver 1041 generates a reception signal sequence with respect to each reception transducer Rw, based on reflected ultrasound obtained by each reception transducer Rw arranged in an array of all or a plurality of the N transducers 101a of the probe 101, in correspondence with a transmission event. The reception transducers Rw are selected by the multiplexer 102. According to the present embodiment, an array center of an array Rwx of reception transducers Rw is selected so as to coincide with an array center of a transmission transducer array (transmission aperture Tx). It is beneficial if a number M of reception transducers Rw is the same as a number of transmission transducers or greater than the number of transmission transducers. Further, the number of the reception transducers Rw may be equal to the total number N of the transducers 101a.

The transmitter 1031 repeats ultrasound transmission while gradually shifting the transmission aperture Tx in an array direction in correspondence with transmission events, performing ultrasound transmission from all of the transducers 101a of the probe 101. The receiver 1041 generates a sequence of reception signals for each reception transducer Rw in correspondence with transmission events, and generated reception signal sequences are stored by the reception signal holding section 1042.

(2) Reception Signal Holding Section 1042

The reception signal holding section 1042 is a computer-readable storage medium and may be, for example, a semiconductor memory or the like. The reception signal holding section 1042 accepts as input a reception signal sequence for each reception transducer from the transmitter 1031 in correspondence with transmission events, and may hold these sequences until an ultrasound image is generated. Further, the reception signal holding section 1042 may be, for example, a hard disk, MO, DVD, DVD-RAM, or the like. Further, the reception signal holding section 1042 may be a storage device that is external and connectable to the ultrasound diagnostic device 100. Further, the reception signal holding section 1042 may be a portion of the data storage 107.

(3) Delay-and-Sum Section 1043

The delay-and-sum section 1043 is a circuit that generates acoustic line signals by performing delay-and-sum processing with respect to reception signal sequences received by reception transducers from observation points, with respect to a plurality of observation points in a calculation target region Bx in a subject, corresponding to transmission events.

Here, the "calculation target region Bx" is a region for which an acoustic line signal is generated, corresponding to one transmission event. Thus, the delay-and-sum section 1043 is a circuit that generates an acoustic line signal of one frame by synthesizing acoustic line signals of observation points in a plurality of calculation target regions Bx generated corresponding to a plurality of transmission events. Here, "frame" refers to a unit of one coherent signal necessary for constructing one ultrasound image. One frame worth of synthesized acoustic line signals is referred to as a "frame acoustic line signal". According to the present embodiment, the calculation target region Bx for which an acoustic line signal is generated in correspondence with a transmission event is a straight line region having a width of one transducer, perpendicular to the transducer array and passing through an array center of the reception aperture Rx. However, the calculation target region Bx is not limited to this example, and may be set as any region included in the ultrasound primary irradiation region Ax.

In FIG. 3, the delay-and-sum section 1043 includes a delay time calculator 10431, a delay time application number determiner 10432, a delay processor 10433, a summer 10434, and a synthesizer 10435. The following describes structure of each element.

i) Delay Time Calculator 10431

The delay time calculator 10431 is a circuit that calculates each delay time for reflected ultrasound to arrive at a reception transducer from a reference observation point PR as a reference delay time, the reference observation point PR being selected from a plurality of observation points P in a region of interest corresponding to an analysis target range in a subject. Here, the "reference observation point PR" is an observation point among observation points P that is a target for delay time calculation. An acoustic line signal with reference to the reference observation point PR is calculated based on a delay time calculated with reference to the observation point. On the other hand, a "dependent observation point PF" is an observation point among observation points P for which a corresponding acoustic line signal is calculated by performing delay-and-sum processing by applying a delay time calculated with respect to the reference observation point PR. In the present description, where observation points P, PR, PF are referenced with indices i, j corresponding to coordinates in an X direction and a Y direction, the notation Pij, PRij, PFij may be used.

Figure 5:
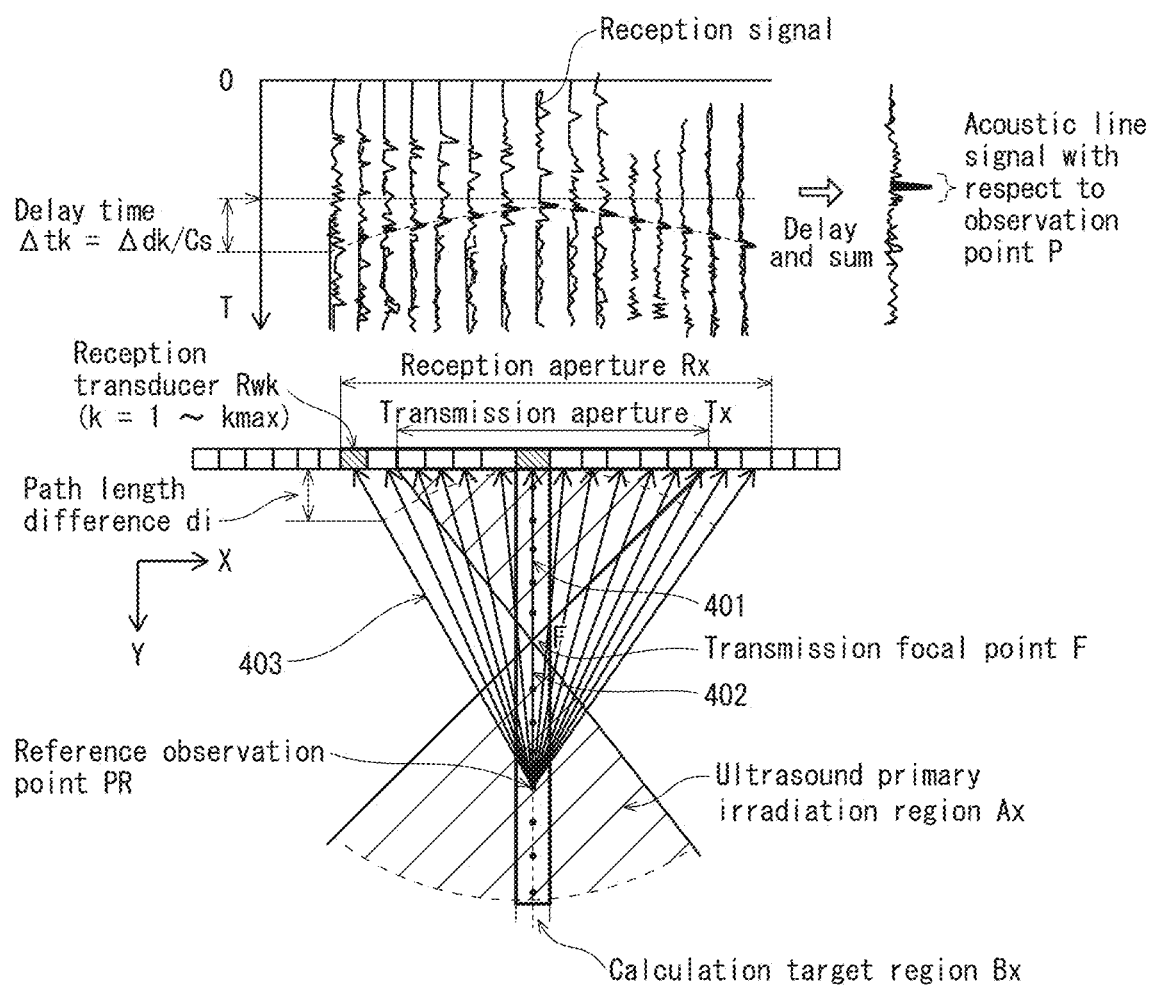
FIG. 5 is a schematic diagram for describing acoustic line signal generation regarding a reference observation point PR in reception beamformer 104.

FIG. 5 is a schematic diagram for describing acoustic line signal generation regarding the reference observation point PR in the delay-and-sum section 1043. A transmission wave radiated from the transmission aperture Tx propagates along path 401, a wavefront thereof converging at the transmission focal point F diffusing again to arrive at observation point P, where a change in acoustic impedance at the observation point P generates a reflected wave, the reflected wave returning to reception transducers Rw of the reception aperture Rx of the probe 101. A length of paths 401+402 to an observation point P via the transmission focal point F, and a length of a path 403 from the observation point P to each reception transducer Rw can be geometrically calculated.

More specifically, the following is a calculation of delay time with respect to the reference observation point PR.

The delay time calculator 10431 calculates an arrival time difference (delay) of reflected ultrasound to each reception transducer Rw by dividing a distance between the reference observation point PR and each reception transducer Rw by a sound velocity value Cs, for each of a plurality of the reference observation points PR in the calculation target region Bx, from reception signal sequences with respect to reception transducers Rw in the reception aperture Rx. More specifically, as illustrated in FIG. 5, the delay time calculator 10431 geometrically calculates length of paths from the reference observation point PR to each reception transducer Rwk (k=1 to kmax), based on information indicating position of the reception transducer Rw and information indicating position of the reference observation point PR, in correspondence with a transmission event. A difference Δdk of path length from the reference observation point PR to each reception transducer Rwk is divided by the sound velocity value Cs to calculate, for each reception transducer Rwk, a delay time Δtk of a reflected wave arriving at each reception transducer Rw from any reference observation point PR.

ii) Delay Time Application Number Determiner 10432

The delay-and-sum section 1043 generates an acoustic line signal by applying a reference delay time to each of the reception transducers Rw with respect to the reference observation point PR and one or more dependent observation points PF that are contiguous with the reference observation point PR in the depth direction. At this time, the reference delay time calculated for the reference observation point PR is applied to the dependent observation points PF that are contiguous with the reference observation point PR in the depth direction. The delay time application number determiner 10432 (hereinafter, also referred to as "application number determiner 10432") determines the number of dependent observation points PF to which the reference delay time of one reference observation point PR is applied.

Figure 6:
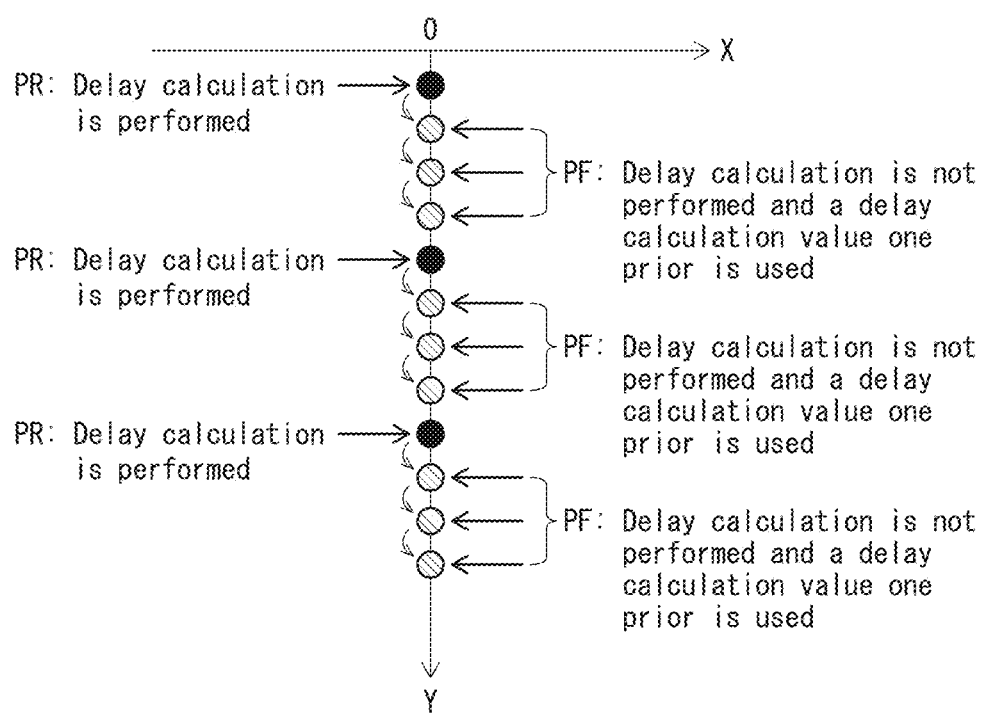
FIG. 6 is a schematic diagram for describing an operation of acoustic line signal generation regarding dependent observation points PF in delay-and-sum section 1043.
Figure 7:
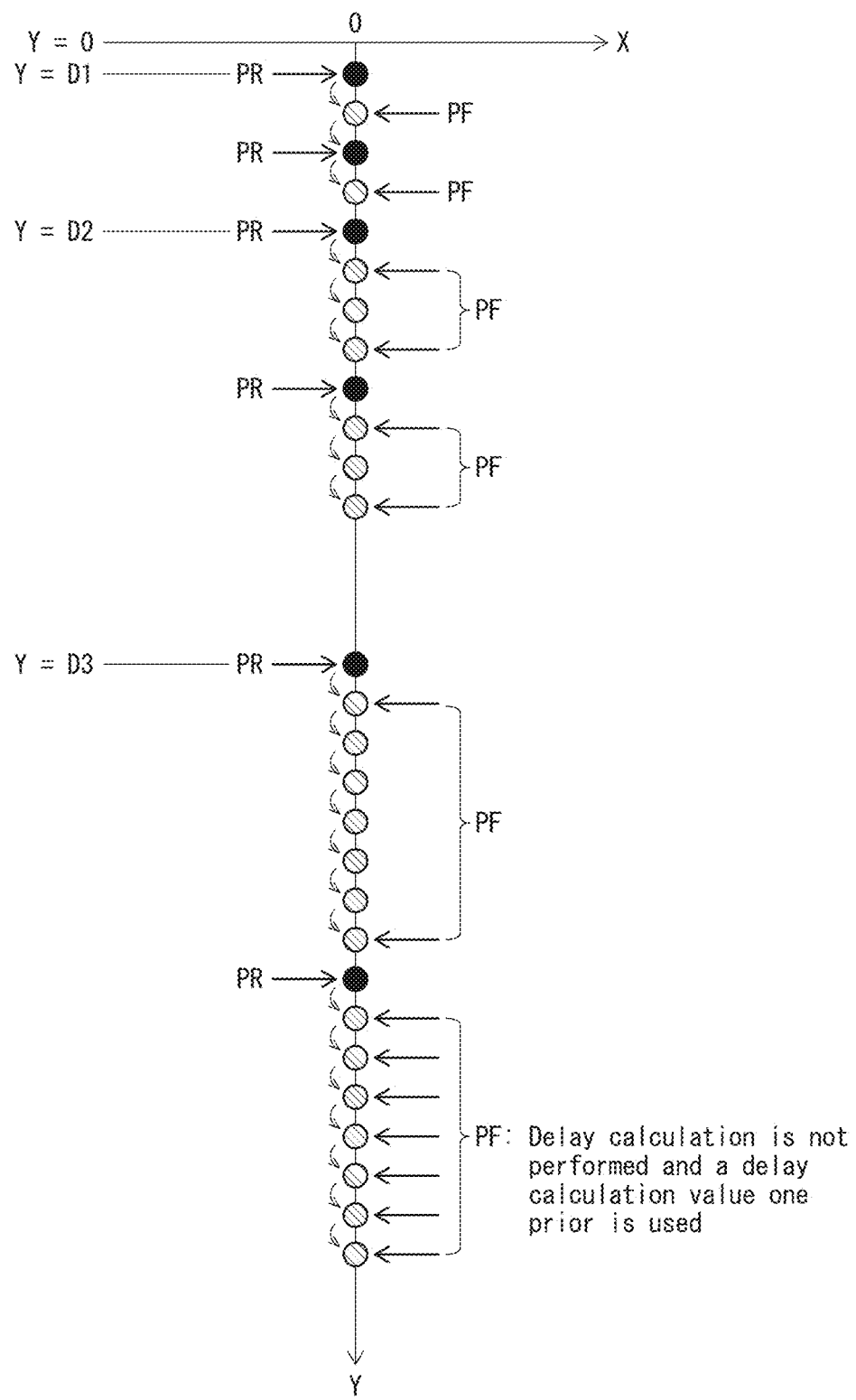
FIG. 7 is a schematic diagram for describing an operation of acoustic line signal generation regarding dependent observation points PF in delay-and-sum section 1043.

FIG. 6 and FIG. 7 are schematic diagrams for describing an operation of acoustic line signal generation regarding observation points P in the delay-and-sum section 1043. In the example illustrated in FIG. 6, the application number determiner 10432 determines the number of dependent observation points PF such that the reference delay time calculated for the reference observation point PR is applied to three dependent observation points PF. In this case, the reference observation points PR and the dependent observation points PF are arranged alternating in the depth direction of the subject in the region of interest. Alternatively, as illustrated in FIG. 7, the application number determiner 10432 may determine the number of dependent observation points PF such that the greater the depth of the subject, the greater the number of dependent observation points PF with respect to one reference observation point PR. In FIG. 7, the reference delay time is applied to one, three, or seven dependent observation points PF in descending order of depth at depths equal to or greater than threshold depths D1, D2, and D3. In this case, the application numbers are 1, 3, and 7. A reason for increasing the number of observation points to which the reference delay time is applied in deeper regions is that as a distance difference from the reference observation point PR to each reception transducer Rwk (k=1 to kmax), i.e., a delay difference, becomes smaller and in a deeper region reflected wave attenuation leads to lower signal to noise ratios than at shallower depths, therefore, even when high density delay-and-sum processing is performed, it becomes difficult to recognize effects of image quality improvement hidden by image quality deterioration due to the attenuation.

In the following description, where operations are described indicating X, Y coordinates of observation points P, PR, PF corresponding to indices i, j, for convenience, the notation P(i,j) may be used without distinguishing between Pij, PRij, and PFij.

Figure 8:
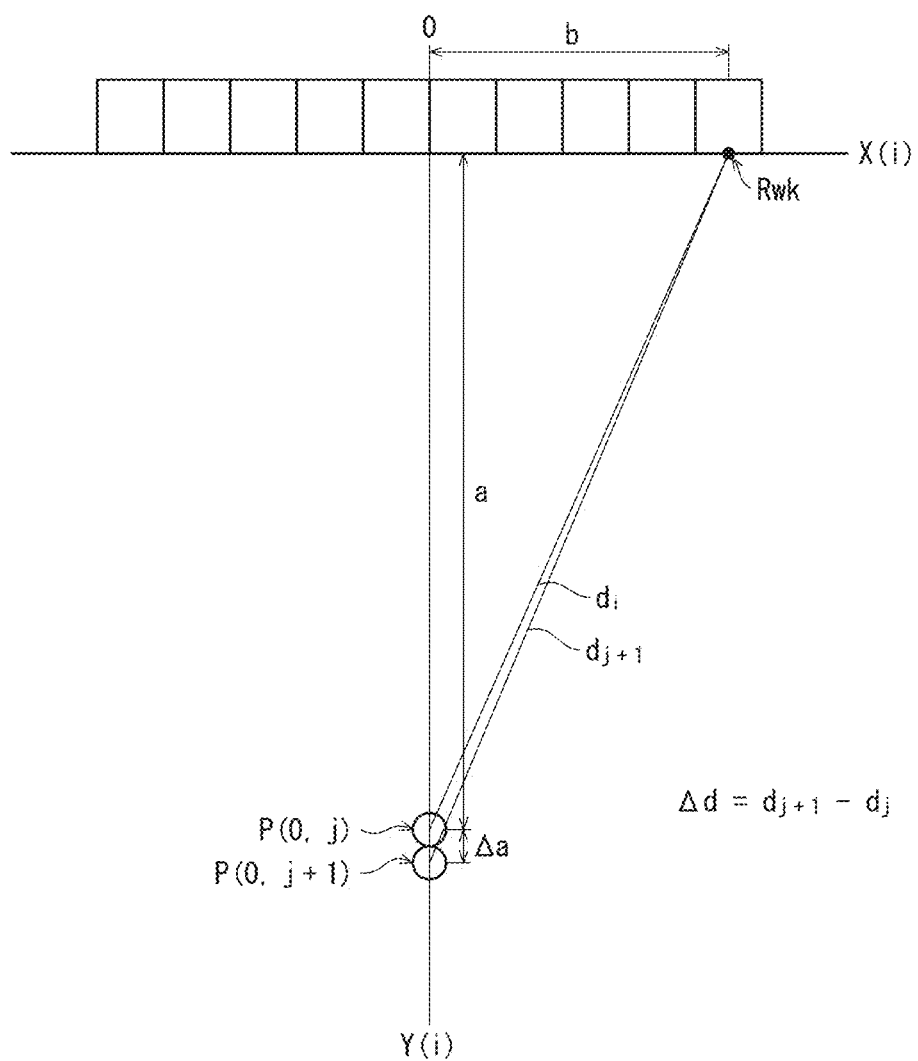
FIG. 8 is a schematic diagram illustrating a difference $\Delta d$ in path length between a reception transducer Rwk and observation points P(0,j) and P(0,j+1) that are adjacent to each other in the depth direction.

FIG. 8 is a schematic diagram illustrating a difference Δd in path length between a reception transducer Rwk and observation points P(0,j) and P(0,j+1) that are adjacent to each other in the depth direction. As an example, the number of reception transducers Rw in the azimuth direction is 128, and a pitch thereof is from 0.2 mm to 0.3 mm. Further, a distance Δa between the observation point P(0,j) and the observation point P(0,j+1) with 60 MHz sampling is, for example, approximately 0.026 mm, and a position of a deepest observation point P is approximately 400 mm. In this case, the larger the depth of the observation points P(0,j), P(0,j+1), the more the difference Δd of path length between the reception transducers Rwk approaches the distance Δa in the depth direction between the observation points P(0,j), P(0,j+1), and delay amount and sampling period have corresponding magnitudes.

Figure 9:
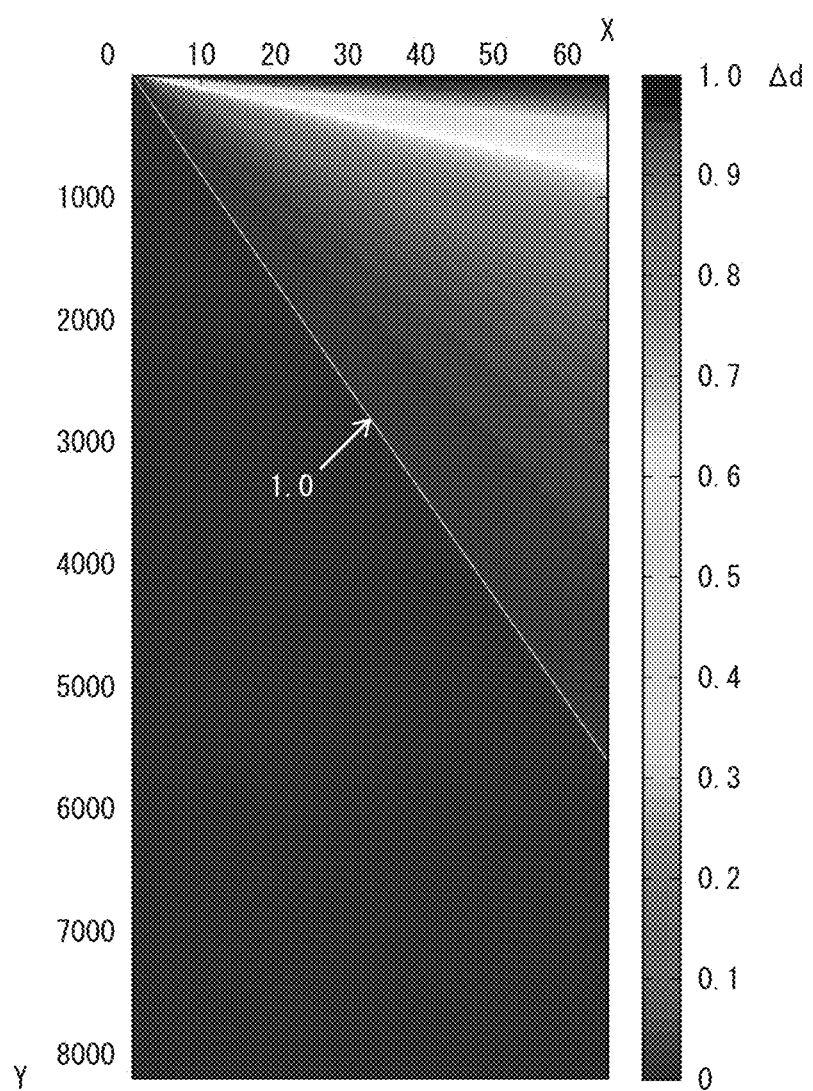
FIG. 9 is a distribution diagram illustrating distribution of the difference $\Delta d$ in path length between a reception transducer Rwk and observation points P(0,j) and P(0,j+1) that are adjacent to each other in the depth direction, in which the vertical axis is depth direction coordinate Y of an observation point P(0,j) and the horizontal axis is an azimuth direction coordinate X of a reception transducer Rw.

FIG. 9 is a distribution diagram illustrating distribution of the difference Δd in path length between a reception transducer Rwk and observation points P(0,j) and P(0,j+1) that are adjacent to each other in the depth direction, in which the vertical axis is depth direction coordinates Y of an observation point P(0,j) and the horizontal axis is azimuth direction coordinates X of a reception transducer Rw. The azimuth direction indicates an element number when X=0 at an array center of the reception transducers Rw, and the depth direction indicates a sampling number at 60 MHz. Scale of Δd is normalized by the sampling period, Δd=1 meaning a delay time Δt of 0, and Δd=0 meaning a delay time Δt corresponding to one sampling period. It can be seen that Δd=1.0 for all reception transducers Rw at depths beyond approximately sample 5500.

FIG. 10 is an enlargement of a range of depth direction coordinates of FIG. 9 from sample 0 to sample 2000, in which Δd values equal to or greater than 0.5 sampling period are increased to 1. As illustrated in FIG. 10, it can be seen that Δd is increased to 1 for all reception transducers Rw at depths beyond approximately sample 600. In this case, even if delay processing calculation is performed for each of observation points P(0,j), P(0,j+1) adjacent in the depth direction, calculation results cannot be reflected in the output. In FIG. 10, DM is a line indicating a typical relationship between depth and the reception aperture Rx in a case in which a dynamic aperture is used that makes size of the reception aperture Rx different according to depth. Thus, it can be seen that in a dynamic aperture use-case, at all depths, for all reception transducers Rw, Δd is increased to 1, and even if delay processing calculation is performed for each observation point P(0,j), P(0,j+1), calculation results cannot be reflected in the output.

Figures 11A, 11B, 11C:
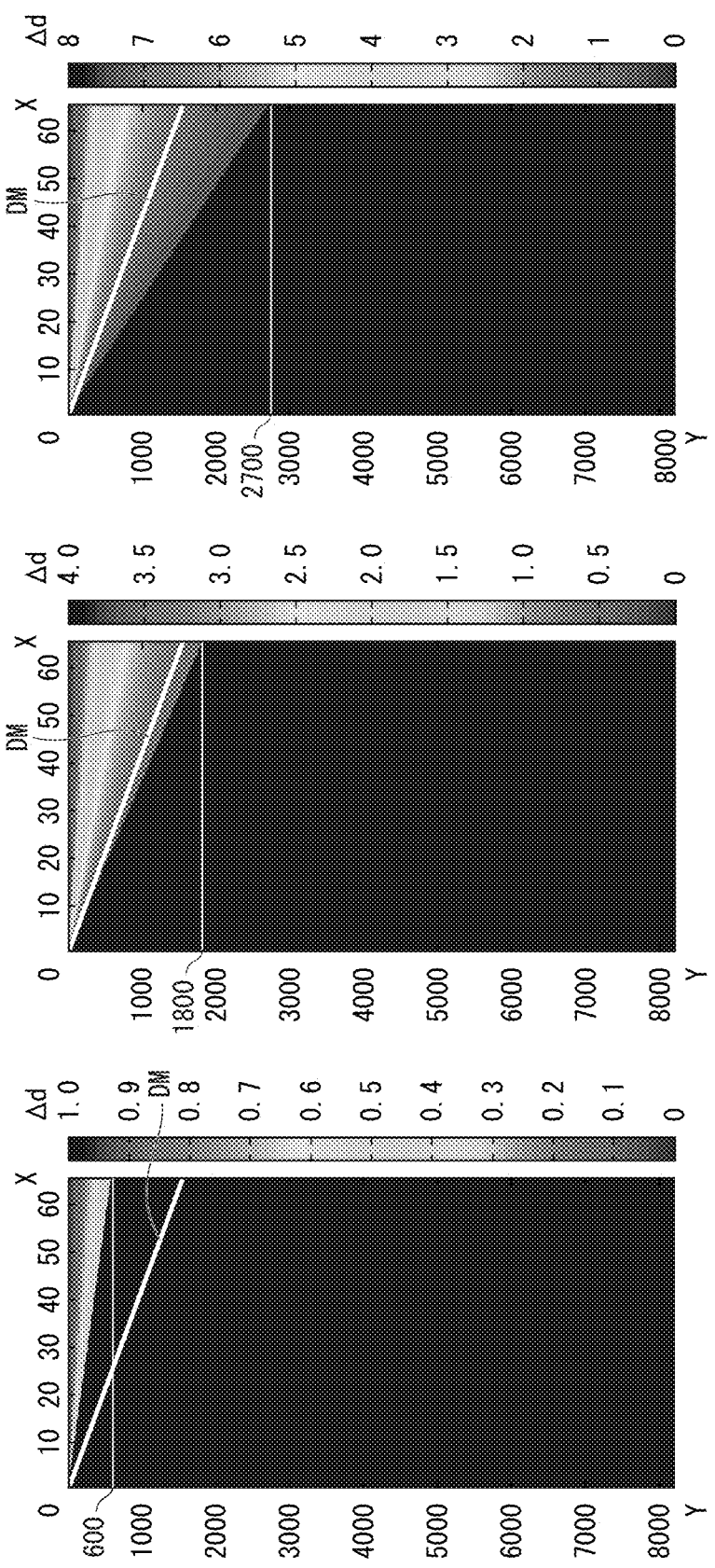
FIGS. 11A, 11B, 11C are distribution diagrams in which $\Delta d$ values equal to or greater than 0.5 are increased to 1.

FIGS. 11A, 11B, 11C are distribution diagrams in which Δd values equal to or greater than a ½ sample period are increased to 1; FIG. 11A illustrates a difference in path length between a reception transducer Rwk and observation points P(0,j) and P(0,j+1) that are adjacent to each other in the depth direction, FIG. 11B illustrates a difference in path length between a reception transducer Rwk and observation points P(0,j) and P(0,j+4) that are 4 away from each other in the depth direction, and FIG. 11C illustrates a difference in path length between a reception transducer Rwk and observation points P(0,j) and P(0,j+8) that are 8 away from each other in the depth direction. That is, FIG. 11A is of a 1 sample period, FIG. 11B is of a 2 sample period, and FIG. 11C is of a 4 sample period. In FIG. 11A, FIG. 11B, and FIG. 11C, DM is a line indicating a typical relationship between depth and the reception aperture Rx in a case in which a dynamic aperture is used.

As can be seen in FIG. 11C, for portions deeper than approximately sample 2700, for all reception transducers, Δd is increased to 8, and even if delay processing calculation is performed for each observation point P(0,j), P(0,j+8) separated by 8 samples in the depth direction, calculation results cannot be reflected in the output.

Similarly, as can be seen in FIG. 11B, for portions deeper than approximately sample 1800, for all reception transducers, Δd is increased to 4, and even if delay processing calculation is performed for each observation point P(0,j), P(0,j+4) separated by 4 samples in the depth direction, calculation results cannot be reflected in the output.

Similarly, as can be seen in FIG. 11A, for portions deeper than approximately sample 600, for all reception transducers, Δd is increased to 1, and even if delay processing calculation is performed for each observation point P(0,j), P(0,j+1) separated by 1 sample in the depth direction, calculation results cannot be reflected in the output.

From the above results, in the depth direction, sampling is performed at every 1 sampling period in a range from 0 to sample 600, every 2 sampling period in a range from approximately sample 600 to sample 1800, every 4 sampling period in a range from approximately sample 1800 to sample 2700, every 8 sampling period in a range from approximately sample 2700 onwards, thereby enabling delay processing calculation results to be reflected in the output without excess or shortfall.

In other words, it is beneficial to gradually increase the sampling period as depth increases to reduce frequency of reference observation points. Thus, it is possible to prevent the inefficiency of calculation results not being reflected in output even when delay processing calculation is performed with respect to each observation point adjacent in the depth direction, and delay processing calculation results can be reflected in the output without excess or shortfall.

iii) Delay Processor 10433

The delay processor 10433 is a circuit that generates an acoustic line signal DS for the reference observation point PR by using the reference delay time with respect to each reception transducer Rw, and also generates an acoustic line signal DS for each of one or more dependent observation points PF that are contiguous in the depth direction from the reference observation point PR by applying the reference delay time with respect to each reception transducer Rw.

First, specification of reception signal values with respect to reference observation points PR is performed as follows.

Based on the arrival time difference (delay) calculated by the delay time calculator 10431, the delay time calculator 10431 calculates an arrival time of a reflected wave from each reference observation point PR to each reception transducer Rw, and the delay processor 10433 identifies a reception signal corresponding to each reception transducer Rw based on arrival times of the reflected wave. More specifically, the delay time calculator 10431 calculates an ultrasound round-trip time to and from the reference observation point PR and a reception transducer Rw nearest to the reference observation point PR, then adds an arrival time difference (delay) calculated by the delay time calculator 10431 in order to calculate an arrival time of the reflected wave to each reception transducer Rw. The delay processor 10433 then reads a reception signal sequence RFk from the reception signal holding section 1042 and specifies reception signal values corresponding to arrival times of the reflected wave to each of the reception transducers Rw. Thus, reception signal values are specified for each of the reception transducers Rwk. The delay processor 10433 performs this processing for all of a plurality of reference observation points PR included in the calculation target region Bx, calculates a delay Δtk for each reception transducer Rwk, and specifies reception signals.

Next, specification of reception signal values with respect to dependent observation points PF is performed as follows.

In the generation of an acoustic line signal with respect to a dependent observation point PF, a delay time of arrival of a reflected wave from the dependent observation point PF to each reception transducer Rw is not calculated. According to the present embodiment, reception signal values corresponding to the reference delay time Δtk are specified with respect to each reception transducer Rwk from a plurality of reception signal sequences RFk corresponding to the reception transducers Rwk, and summing is performed for a plurality of reception transducers Rwk (k=1 to kmax).

More specifically, an ultrasound round-trip time between the dependent observation point PF and a reception transducer Rw nearest to the dependent observation point PF is calculated, and approximated reflected wave arrival times are calculated by adding a reference delay time Δtk for each reception transducer Rwk to the ultrasound round-trip time. The delay processor 10433 then reads a reception signal sequence RFk from the reception signal holding section 1042 and specifies reception signal values corresponding to approximated reflected wave arrival times from a plurality of reception signal sequences RFk corresponding to the reception transducers Rw. Thus, reception signal values are specified for each of the reception transducers Rwk. At this time, calculation of the ultrasound round-trip time between the dependent observation point PF and the reception transducer Rw nearest to the dependent observation point PF may be performed by adding or subtracting an ultrasound round-trip time between the reference observation point PR and the dependent observation point PF to or from the ultrasound round-trip time between the reference observation point PR and the reception transducer Rw nearest the reference observation point PR. Further, an ultrasound round-trip time between two points may be calculated as a round-trip distance between two points divided by a sound velocity value Cs. This processing is performed for all reception transducers Rwk, and a reception signal is specified for each reception transducer Rwk.

Details of operations of the delay processor 10433 are described later.

iv) Summer 10434

The summer 10434 is a circuit that accepts as input reception signals identified as corresponding to reception transducers Rwk outputted from the delay processor 10433 and sums the reception signals to generate acoustic line signals subject to delay-and-sum processing with respect to observation points P. Alternatively, a configuration may be used in which reception signals identified as corresponding to reception transducers Rw are multiplied by a weighting sequence with respect to the reception transducers Rw (reception apodization) and summed to generate acoustic line signals with respect to observation points P. In this case, it is beneficial that the weighting sequence has a symmetric distribution centered on the transmission focal point F so that weight of a transducer located at a center in the array direction of the reception aperture Rx is a maximum weight. A distribution shape of the weighting sequence can use a Hamming window, a Hann window, a rectangular window, or the like, and the distribution shape is not limited in any particular way.

The delay processor 10433 compensates for delay times of reception signals detected by reception transducers Rw located in the reception aperture Rx and the summer 10434 performs summing processing, and therefore reception signals received by the reception transducers Rw based on a reflected wave from an observation point P are superimposed, increasing signal to noise ratio, and reception signals from the observation point P can be extracted.

It is possible to generate acoustic line signals for all observation points P in the target calculation region Bx from the processing accompanying one transmission event. In correspondence with transmission events, the transmission aperture Tx is gradually shifted in the array direction while ultrasound transmission is repeatedly performed, so that ultrasound transmission is performed from all of the transducers 101a of the probe 101, and acoustic line signals of the calculation target regions Bx generated in correspondence with the transmission events are gradually outputted to the synthesizer 10435.

v) Synthesizer 10435

The synthesizer 10435 is a circuit that synthesizes a frame acoustic line signal from acoustic line signals of the calculation target region Bx generated in correspondence with transmission events. The synthesizer 10435 gradually inputs from the summer 10434 acoustic line signals generated with respect to a plurality of observation points P in the calculation target region Bx in correspondence with transmission events, and superimposes the acoustic line signals with respect to each observation point P by using position of the observation points P for which acoustic line signals are acquired as indices, in order to synthesize a frame acoustic line signal. As described above, ultrasound transmission is sequentially performed by gradually shifting the transducers used in the transmission transducer array (transmission aperture Tx) in correspondence with transmission events. Thus, the calculation target region Bx based on different transmission events also gradually shifts position in the same direction each transmission event. By superimposition with positions of observation points P for which acoustic line signals are acquired as indices, a frame acoustic line signal is synthesized that covers all calculation target regions Bx.

A synthesized frame acoustic line signal is outputted to the ultrasound image generator 105.

<Operations>

The following describes operations of the ultrasound signal processing device 150 configured as described above.

Figure 12:
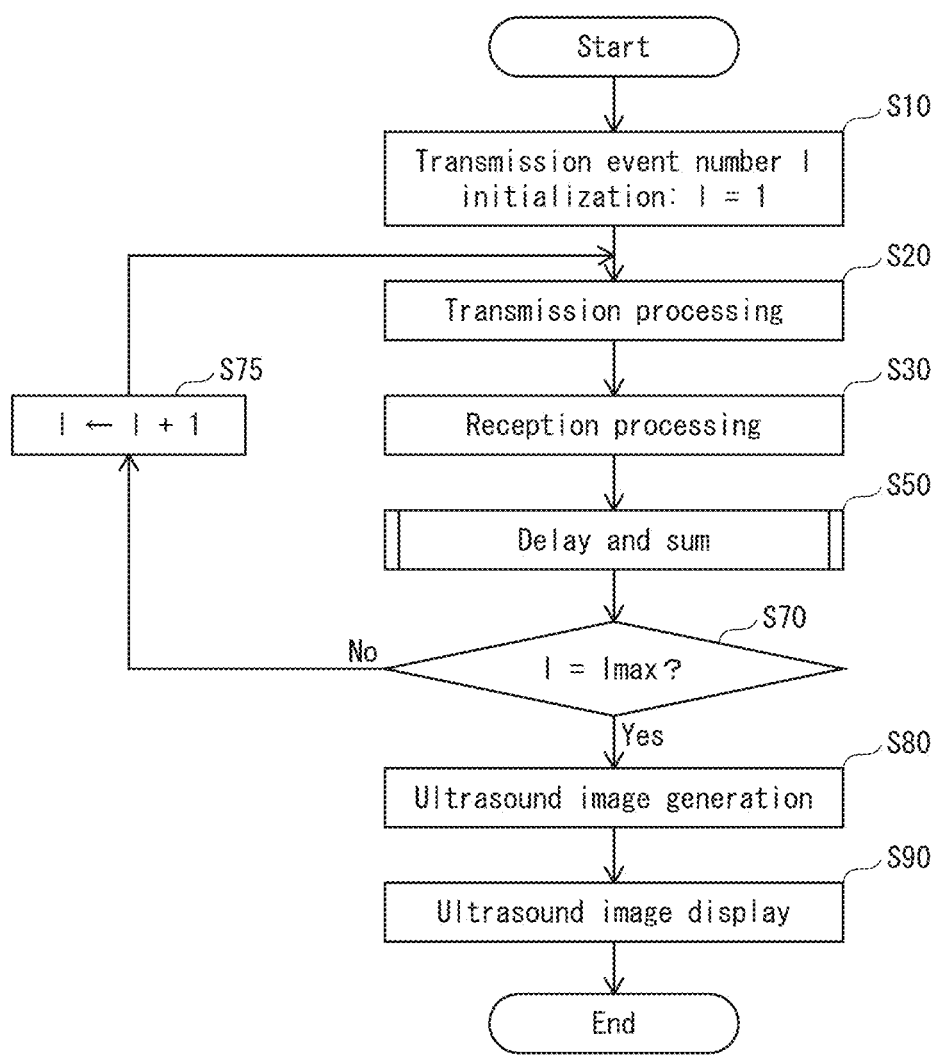
FIG. 12 is a flowchart illustrating processing in an ultrasound signal processing device 150.

FIG. 12 is a flowchart illustrating processing in the ultrasound signal processing device 150.

First, after the start of ultrasound examination, when generating a first frame ultrasound image, an index 1 representing a transmission event number is initialized (step S10).

Next, in step S20, the transmitter 1031 performs transmission processing supplying a transmission signal for causing transmission of an ultrasound beam to each transducer included in a transmission aperture Tx among the transducers 101a of the probe 101 (a transmission event).

Next, in step S30, the receiver 1041 generates reception signals based on electrical signals obtained from reception of a reflected ultrasound wave by the probe 101 and outputs to the reception signal holding section 1042, which holds the reception signals.

Next, in step S50, the delay-and-sum section 1043 generates one frame of acoustic line signals by generating acoustic line signals for all observation points in a region of interest in the subject for which an ultrasound image is to be generated.

Figure 13:
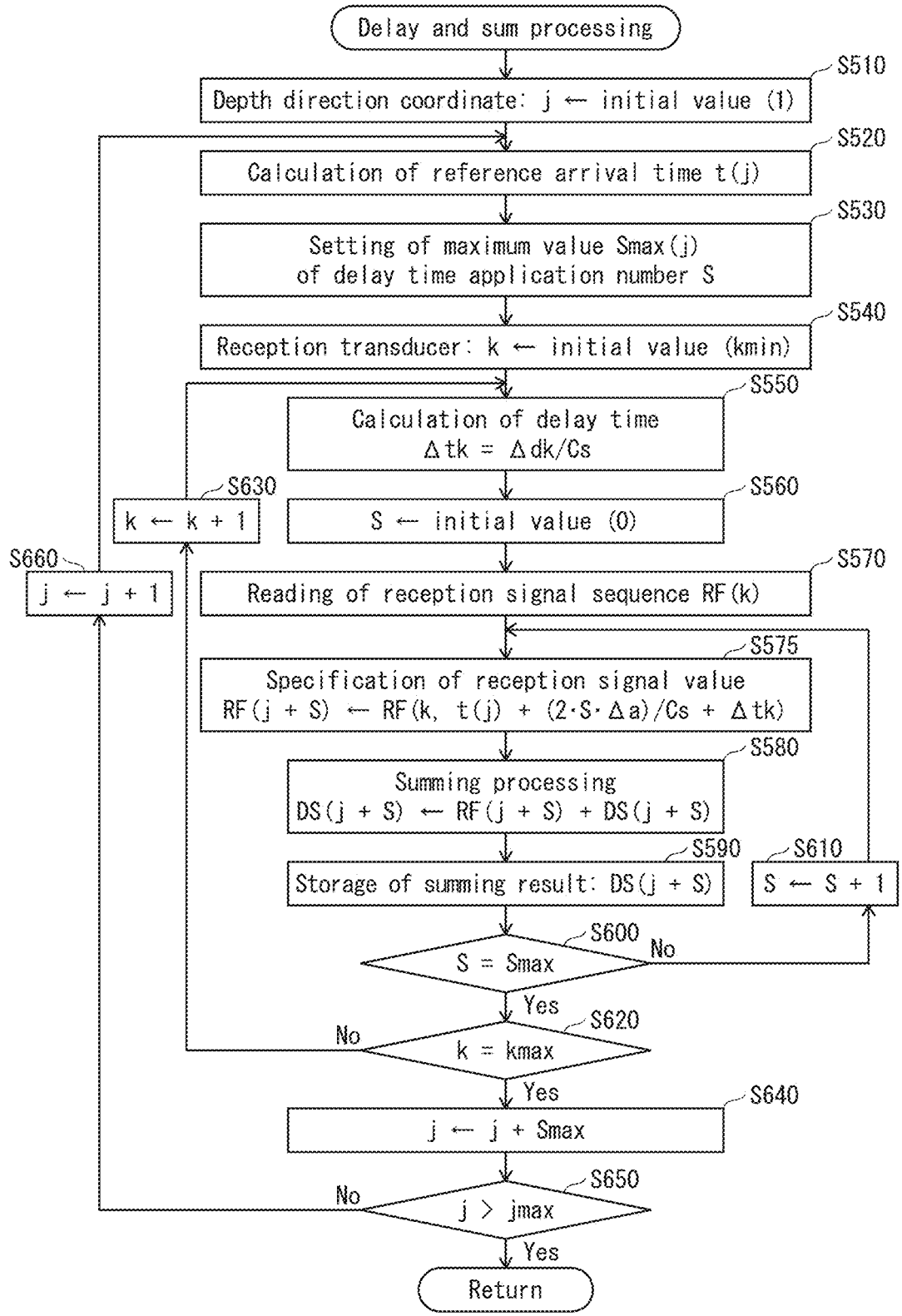
FIG. 13 is a flowchart illustrating details of delay-and-sum processing (step S50) in FIG. 12.
Figure 14:
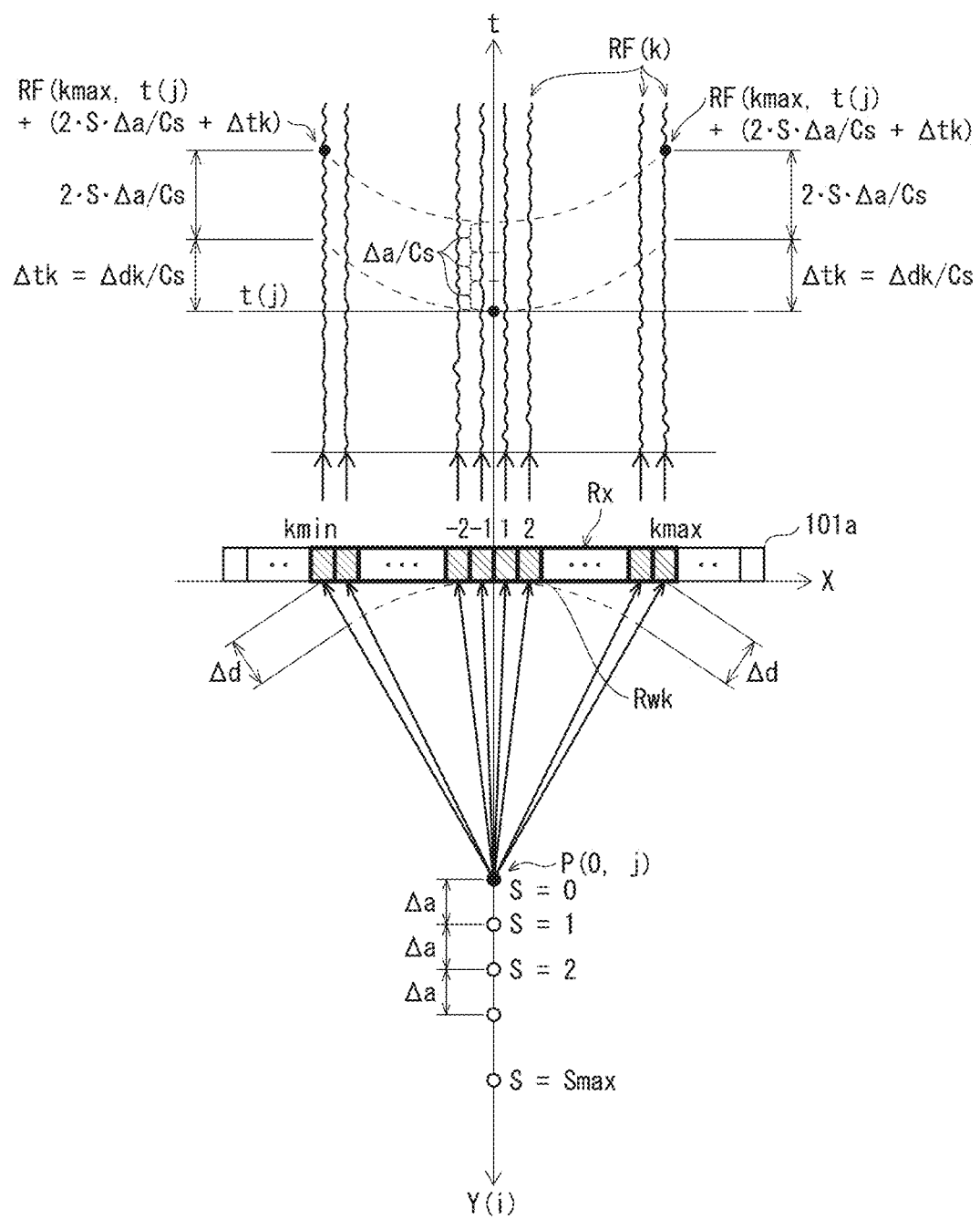
FIG. 14 is a schematic diagram for describing an operation of acoustic line signal generation regarding dependent observation points PF in delay-and-sum section 1043.

The following describes in detail the processing of step S50. FIG. 13 is a flowchart illustrating details of delay-and-sum processing (step S50). FIG. 14 is a schematic diagram for describing an operation of acoustic line signal generation regarding dependent observation points PF in the delay-and-sum section 1043.

In this example, it is assumed that the array center of the transmission aperture Tx and the array center of the reception aperture Rx coincide, and in the region of interest corresponding to an analysis target range of the subject, where X represents an azimuth direction coordinate and Y represents a depth direction coordinate, an observation point P(0,Y) is set on a beam center line parallel to the depth direction and passing through a center of the reception aperture Rx for each transmission event, in order to calculate acoustic line signals.

First, in step S510, an index j representing the depth direction coordinate Y of the observation point P(0,j) is set to an initial value (1), and a reference arrival time t(j) is calculated (step S520). The reference arrival time t(j) is the time required for ultrasound to make a round-trip between the observation point P(0,j) and the reception transducer Rw positioned at an array center of the reception aperture Rx.

Next, a maximum value Smax(j) of a delay time application number S is set (step S530). The delay time application number S is the number of times the reference delay time t(j) calculated for the observation point P(0,j) is applied with respect to observation points P(0,j+S) that are contiguous in the depth direction from the observation point P(0,j). At this time, the maximum value Smax(j) of the delay time application number S may be set differently according to a value of depth j of the subject. For example, Smax(j) may be set larger as the value of j is larger. Further, a threshold for j may be provided, and when j exceeds the threshold, Smax(j) may be increased.

Next, an index k for identifying the reception transducers Rw is set to an initial value (step S540). In this example, the initial value is set to a minimum value kmin of reception transducers Rw(kmin to kmax) included in the reception aperture Rx.

Next, the delay time calculator 10431 calculates the delay time Δtk for arrival of a reflected wave from the observation point P(0,j) to the reception transducer Rwk. More specifically, as illustrated in FIG. 5, the delay time calculator 10431 geometrically calculates a path length from the observation point P(0,j) to the reception transducers Rwk, based on information indicating position of the reception transducers Rwk and information indicating position of the observation point P(0,j). Then, the delay time calculator 10431 divides path length differences Δdk from the observation point P(0,j) to the reception transducers Rwk by the sound velocity value Cs, to calculate the delay time Δtk for the reflected wave to arrive at each reception transducer Rwk from the observation point P(0,j).

Next, the delay processor 10433 sets the delay time application number S to an initial value (0) (step S560), reads a reception signal sequence RF(k) from the reception signal holding section 1042 (step S570), specifies a reception signal value RF(k,t(j)+(2·S·Δa)/Cs+Δtk) in the reception signal sequence RF(k), and sets it as a reception signal value RF(J+S) (step S575). Here, Δa, as illustrated in FIG. 14, is a path length difference between observation point P(0,j+S−1) and observation point P(0,j+S). This example is of a first iteration, and therefore S=0, and therefore RF(j+S) is set as RF(k,t(j)+Δtk).

Next, the summer 10434 is also processing the first iteration, and therefore the reception signal value RF(j+S) is replaced by an acoustic line signal DS(j+S) (step S580), and the acoustic line signal DS(j+S) is stored in the summing register (step S590).

Then, whether or not the delay time application number S is the maximum value Smax is determined (step S600), and if not the maximum value Smax, S is incremented (step S610) and processing returns to step S575. In step S575, a reception signal value RF(k,t(j)+(2·S·Δa)/Cs+Δtk) in the reception signal sequence RF(k) is specified and set as a reception signal value RF(j+S), and a sum of the reception signal value RF(j+S) the acoustic line signal DS(j+S) stored in the summing register is calculated (step S580), the new acoustic line signal DS(j+S) being stored in the summing register (step S590).

In step S600, if the delay time application number S is the maximum value Smax, whether or not the index k identifying a reception transducer Rw is the maximum value kmax is determined (step S620), and if not the maximum value kmax, k is incremented (step S630) and processing returns to step S550. At this stage, acoustic line signal DS(j+S) (S=0 to Smax) is stored. In step S550, by specifying a reception signal value RF(j+S) (S=0 to Smax) for an adjacent reception transducer Rwk+1, the acoustic line signal DS(j+S) (S=0 to Smax) is updated (step S590).

In step S620, if k is the maximum value kmax of reception transducers Rw in the reception aperture Rx, the acoustic line signal DS(j+S) (S=0 to Smax) with respect to the observation point P (0,j+S) (S=0 to Smax) is calculated, j is replaced by j+Smax (step S640), and whether or not j exceeds a maximum value jmax is determined (step S640). If j does not exceed the maximum value jmax, j is incremented (step S660) and processing returns to step S520. If j exceeds the maximum value jmax, processing returns to step S50.

Next, returning to FIG. 12, whether or not the transmission event number 1 is equal to a maximum value lmax is determined (step S70), in order to judge whether or not ultrasound transmission is complete from all the transducers 101a of the probe 101. If not complete, 1 is incremented (step S75), processing returns to step S20, and a transmission event is performed with a gradual shift in the array direction of the transmission aperture Tx. If complete, processing proceeds to step S80.

Next, in step S80, the ultrasound image generator 105 subjects one frame of acoustic line signals outputted from the delay-and-sum section 1043 to processing such as envelope detection, logarithmic compression, and the like to perform luminance conversion, and subjects a resulting luminance signal to coordinate transformation into an orthogonal coordinate system in order to generate an ultrasound image (B mode image) of one frame.

Next, in step S90, the display 106 displays on a display screen the ultrasound image of one frame outputted from the ultrasound image generator 105, and the ultrasound signal processing operation is complete.

<Brief Summary>

The ultrasound signal processing device 150 pertaining to Embodiment 1 as described above includes: the transmitter 1031 that causes an array of transmission transducers Tx selected from the transducers 101a to transmit ultrasound beams; the receiver 1041 that, based on reflected waves received by an array of reception transducers Rwk, generates reception signal sequences RFk corresponding to the reception transducers Rwk; and a delay-and-sum section 1043 that, for a reference observation point PRij selected from observation points Pij in a region of interest corresponding to an analysis target range of the subject, (i) calculates delay times of reflected wave arrival to each of the reception transducers Rwk from the reference observation point PRij as reference delay times Δtk, and (ii) generates acoustic line signals DS by using the reference delay times Δtk corresponding to the reception transducers Rwk, and for one or more dependent observation points PFij in the region of interest that are contiguous in a depth direction from the reference observation point PRij, (iii) generates acoustic line signals DS by applying the reference delay times Δtk corresponding to the reception transducers Rwk.

According to this configuration, a calculation load of delay processing in delay-and-sum processing can be reduced while suppressing a decrease in spatial resolution and signal to noise ratio of a frame acoustic line signal. As a result, it is possible to reduce a calculation load of delay time calculation processing, which is a relatively large portion of delay-and-sum processing, thereby reducing an overall calculation load of the delay-and-sum processing.

According to at least one embodiment, the delay-and-sum section 1043 generates the acoustic line signals with respect to the reference observation point PRij by specifying reception signal values corresponding to the reference delay times Δtk corresponding to the reception transducers Rwk from reception signal sequences RFk corresponding to the reception transducers Rwk, and performing summing with respect to the reception transducers Rwk, and the delay-and-sum section 1043 generates the acoustic line signals with respect to the one or more dependent observation points PFij by specifying reception signal values corresponding to the reference delay times Δtk corresponding to the reception transducers Rwk from reception signal sequences RFk corresponding to the reception transducers Rwk, and performing summing with respect to the reception transducers Rwk.

According to this configuration, it is possible to reduce a calculation load required for delay time calculation with respect to a dependent observation point.

According to at least one embodiment, the delay-and-sum section 1043 generates the acoustic line signals DS with respect to the reference observation point PRij by calculating a reference ultrasound round-trip time between the reference observation point PRij and a reception transducer Rwk nearest to the reference observation point PRij, calculating reflected wave arrival times that are each a sum of the reference ultrasound round-trip time and the reference delay time Δtk corresponding to the reception transducer Rwk, specifying reception signal values obtained from the reflected wave arrival times from reception signal sequences RFk corresponding to the reception transducers Rwk, and performing summing with respect to the reception transducers Rwk, and the delay-and-sum section 1043 generates the acoustic line signals DS with respect to each of the one or more dependent observation points PFij by calculating an ultrasound round-trip time between the dependent observation point PFij and a reception transducer Rwk nearest to the dependent observation point PFij, calculating approximate reflected wave arrival times that are each a sum of the reference ultrasound round-trip time and the reference delay time Δtk corresponding to the reception transducer Rwk, specifying reception signal values obtained from the approximate reflected wave arrival time from reception signal sequences RFk corresponding to the reception transducers Rwk, and performing summing with respect to the reception transducers Rwk.

According to this configuration, it is possible to realize a simple calculation method of applying a reference delay time to delay times of dependent observation points, and to configure an ultrasound signal processing device that can reduce a calculation load of delay processing with respect to the dependent observation points.

Embodiment 2

According to the ultrasound signal processing device 150 pertaining to Embodiment 1, the delay-and-sum section 1043, in correspondence with a transmission event, is configured to set a calculation target region Bx as a rectilinear region that passes through an array center of the reception aperture Rx, is perpendicular to the transducer array, and has a width of a single transducer. Further, the delay-and-sum section 1043 is configured to generate acoustic line signals by performing delay-and-sum with respect to reception signal sequences received by reception transducers from a plurality of observation points in the calculation target region Bx. However, the calculation target region Bx is not limited to this example, and may be set as any region included in the ultrasound primary irradiation region Ax. According to the ultrasound signal processing device pertaining to Embodiment 2, the calculation target range Bx is set to a range substantially equal to the ultrasound primary irradiation region Ax, which has an hourglass shape, and acoustic line signals are generated in correspondence with a transmission event for a plurality of observation points distributed in the calculation target region Bx that has an hourglass shape, which is a different configuration from that of Embodiment 1. According to this method, by performing delay control taking into account both a propagation path of transmitted ultrasound and an arrival time of a reflected wave propagating according to the propagation path to a transducer, reception beamforming can be performed that reflects ultrasound reflected from the ultrasound primary radiation region from positions outside the immediate vicinity of a transmission focal point. As a result, acoustic line signals can be generated with respect to an entire ultrasound primary irradiation region from one ultrasound transmission event. Further, in the ultrasound signal processing device pertaining to Embodiment 2, a configuration is adopted of using a synthetic aperture method to generate one frame of acoustic line signals by synthesizing a plurality of reception signals with respect to the same observation point, obtained from a plurality of transmission events, by using coordinates of observation points as a reference. Thus, a high spatial resolution and high signal to noise ratio ultrasound image can be obtained.

<Overview>

The ultrasound signal processing device pertaining to Embodiment 2 is different from the ultrasound signal processing device 150 pertaining to Embodiment 1 in terms of processing operations in a delay-and-sum section, but has the same structure as the ultrasound signal processing device 150 illustrated in FIG. 1 and FIG. 3.

The following is an overview of differences in processing in the delay-and-sum section of the ultrasound signal processing device pertaining to Embodiment 2.

According to the transmitter 1031 pertaining to Embodiment 2, the ultrasound primary irradiation region Ax irradiated by an ultrasound beam in a subject is the same as the region of the ultrasound signal processing device 150 illustrated in FIG. 2.

According to the ultrasound signal processing device pertaining to Embodiment 2, a range of the calculation target region Bx for which acoustic line signals are generated each transmission event is different from a region according to the ultrasound signal processing device 150 as illustrated in FIG. 5. The delay-and-sum section 1043 pertaining to Embodiment 2 generates acoustic line signals with respect to a plurality of observation points Pij in the calculation target region Bx that has the same range as the ultrasound primary irradiation region Ax for each transmission event.

Further, according to the delay-and-sum section 1043 pertaining to Embodiment 2, observation points Pij are classified into reference observation points PRij that are targets for reference delay time calculation and dependent observation points PFij to which the reference delay time is applied in delay-and-sum processing.

1. Delay-and-Sum Processing with Respect to Reference Observation Point PR

Figure 15:
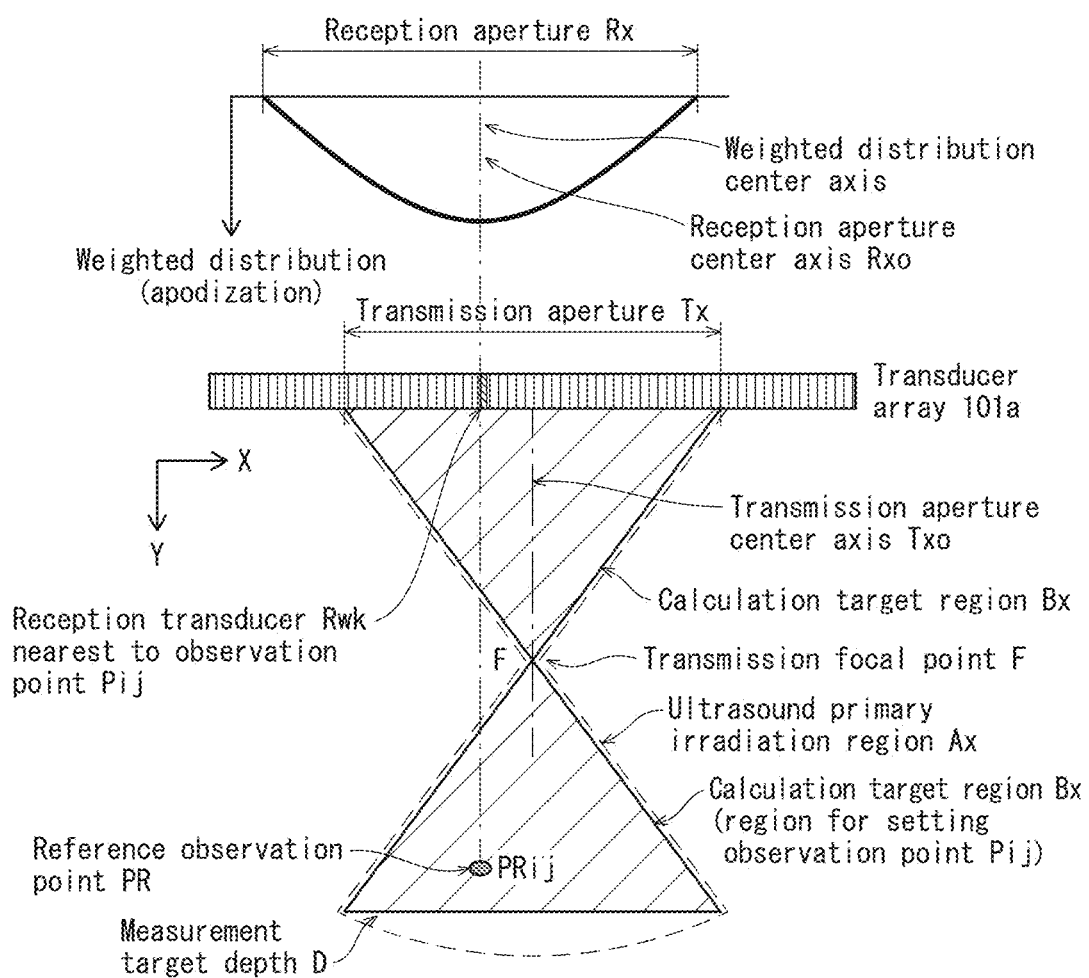
FIG. 15 is a schematic diagram illustrating a relationship between a transmission aperture Tx and a reception aperture Rx set by the reception beamformer 104 of an ultrasound signal processing device pertaining to Embodiment 2.

The delay-and-sum section 1043 performs delay-and-sum processing with respect to a reference observation point PRij in order to calculate a reference delay time. At this time, the delay-and-sum section 1043 selects a reception aperture Rx transducer array so that an array center coincides with the reception transducer Rwk that is spatially closest to the observation point PRij. FIG. 15 is a schematic diagram illustrating a relationship between a reception aperture Rx and a transmission aperture Tx as set in Embodiment 2. As illustrated in FIG. 15, a transducer array constituting the reception aperture Rx transducer array is selected such that an array center of the reception aperture Rx transducer array coincides with a reception transducer Rwk that is spatially closest to an observation point PRij. Thus, even for different transmission events, in processing generating acoustic line signals for an observation point PRij in the same position, delay-and-sum is performed based on reception signals acquired by the same reception transducer Rwk in the reception aperture Rx.

Figure 16A:
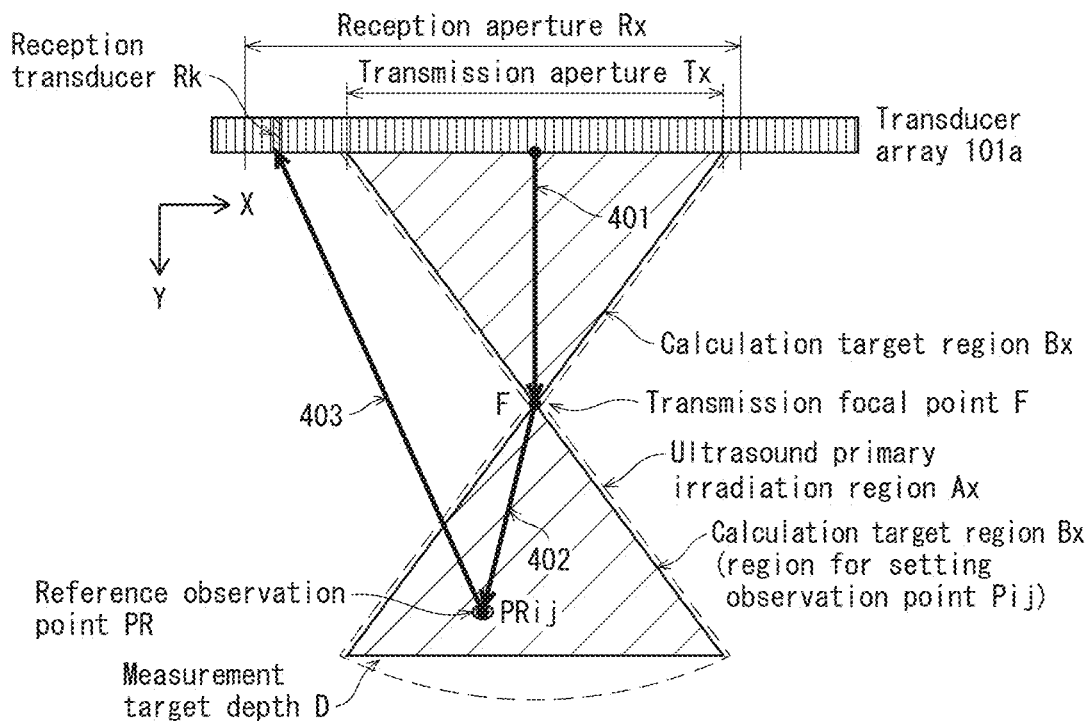
FIGS. 16A and 16B are schematic diagrams for describing propagation paths of ultrasound emitted from a transmission aperture Tx, reflected at an observation point Pij at any position in a calculation target region Bx, and arriving at a reception transducer Rk located in a reception aperture Rx, as calculated by a delay time calculator 10431 pertaining to Embodiment 2.
Figure 16B:
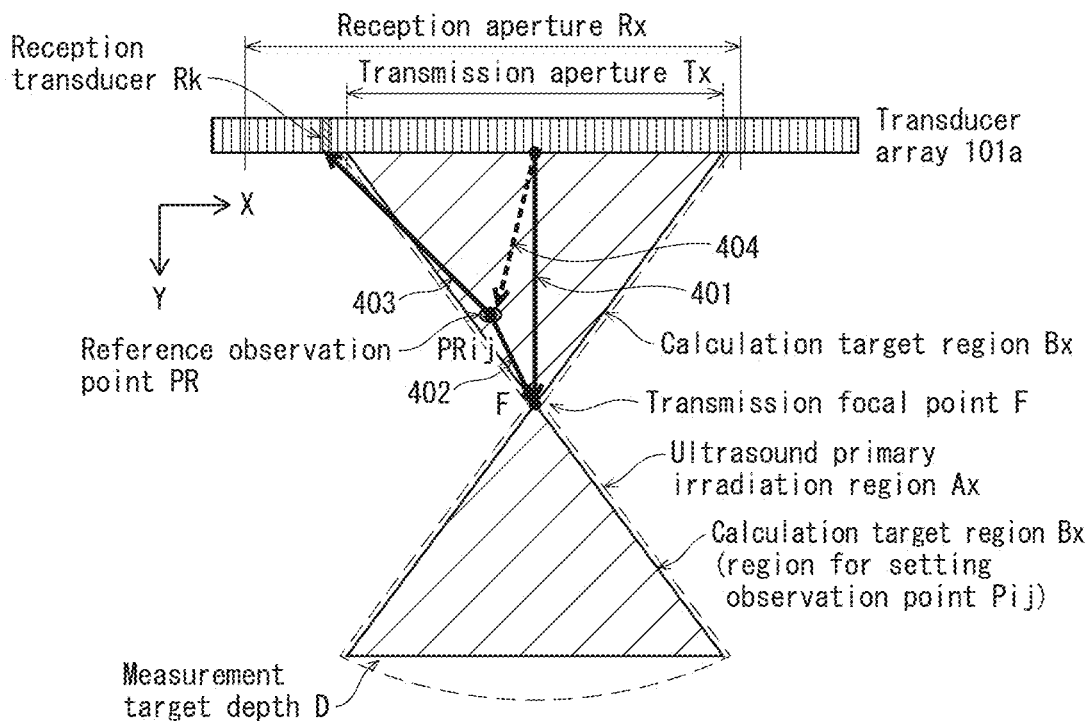

FIGS. 16A and 16B are schematic diagrams for describing propagation paths of ultrasound emitted from a transmission aperture Tx, reflected at an observation point PRij at any position in a calculation target region Bx, and arriving at a reception transducer Rk located in a reception aperture Rx, as calculated by the delay time calculator 10431 pertaining to Embodiment 2. FIG. 16A illustrating an observation point PRij deeper than a focal depth, and FIG. 16B illustrating an observation point PRij at a depth equal to or less than the focal depth.

First, a transmitted wave emitted from the transmission aperture Tx has a wavefront that propagates along a path 401 and converges at a transmission focal point F, then diffuses again. The transmitted wave reaches an observation point PRij while converging or diffusing, a reflected wave is generated at the observation point PRij if there is a change in acoustic impedance, and the reflected wave returns to a reception transducer Rk in the reception aperture Rx of the probe 101. The transmission focal point F is defined as a design value of the transmission beamformer 103, and therefore length of a path 402 between the transmission focal point F and any observation point PRij can be geometrically calculated.

A method of calculating transmission time is described in more detail below.

Initially, as illustrated in FIG. 16A, when the observation point PRij is deeper than the focal depth, a transmission wave radiated from the transmission aperture Tx is calculated as having reached the transmission focal point F via the path 401 and the observation point PRij from the transmission focal point F via the path 402. Accordingly, the transmission time is a sum of time taken for the transmission wave to propagate along the path 401 and to propagate along the path 402. More specifically, for example, the transmission time can be obtained by dividing a sum of length of the path 401 and length of the path 402 by a propagation speed of ultrasound in a subject.

On the other hand, as illustrated in FIG. 16B, when the depth of the observation point PRij is equal to or less than the focal depth, calculation is performed assuming that for a transmission wave radiated from the transmission aperture Tx, a time at which the transmission wave arrives at the transmission focal point F via the path 401 is the same as a time at which the transmission wave arrives at the transmission focal point F from the observation point PRij via the path 402 after arriving at the observation point PRij via a path 404. That is, a value obtained by subtracting the time for a transmission wave to propagate along the path 402 from the time to propagate along the path 401 becomes the transmission time. More specifically, for example, the transmission time can be obtained by dividing a path length difference obtained by subtracting length of the path 402 from length of the path 401 by a propagation speed of ultrasound in a subject.

Next is a description of a method of calculating reception time.

Figure 17:
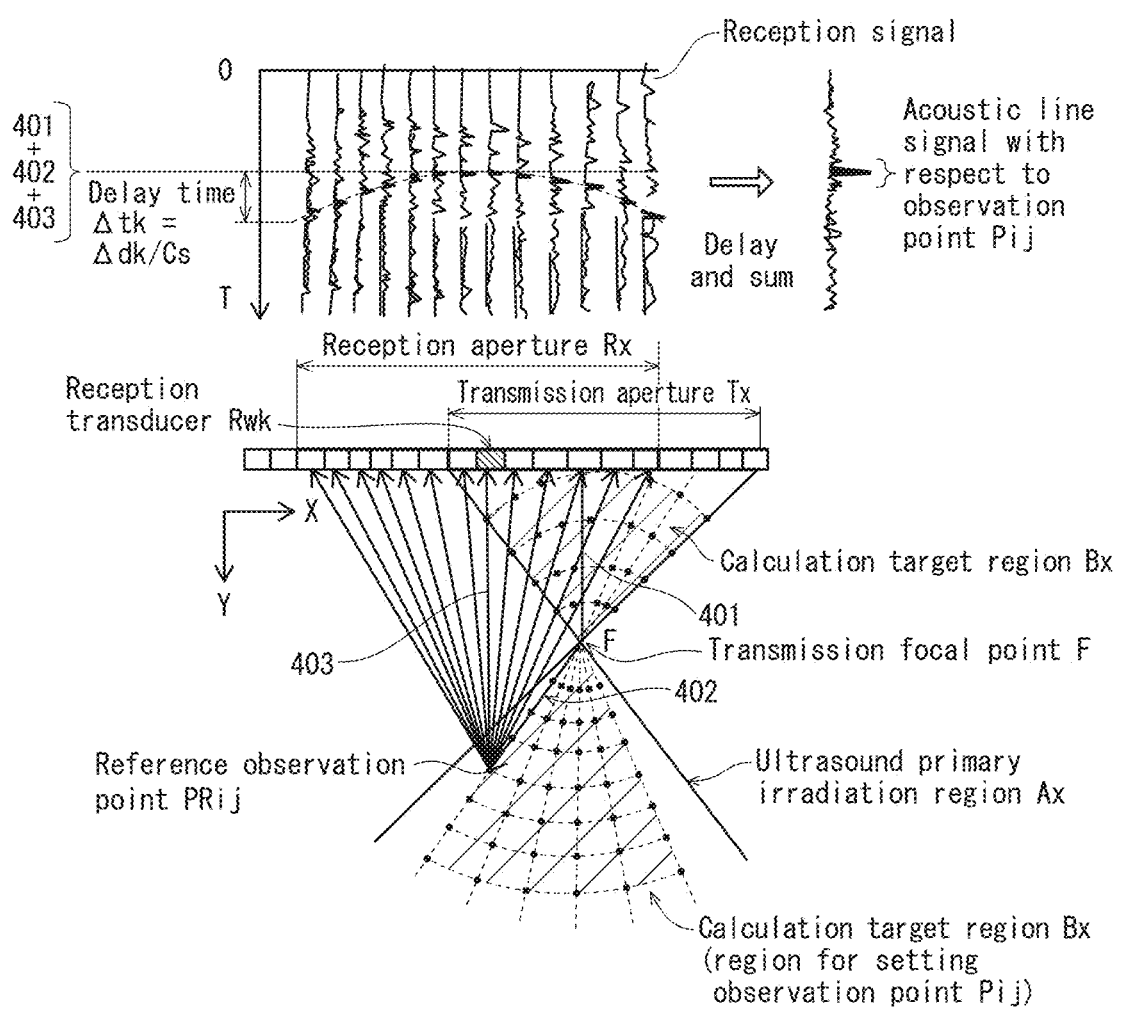
FIG. 17 is a schematic diagram for describing acoustic line signal generation regarding a reference observation point PRij in reception beamformer 104 pertaining to Embodiment 2.

FIG. 17 is a schematic diagram for describing an operation of acoustic line signal generation regarding a reference observation point PRij in the delay-and-sum section 1043. A transmission wave radiated from the transmission aperture Tx propagates along path 401, a wavefront thereof converging at the transmission focal point F diffusing again to arrive at the reference observation point PRij, where a change in acoustic impedance at the reference observation point PRij generates a reflected wave, the reflected wave returning to reception transducers Rwk of the reception aperture Rx of the probe 101. A length of the paths 401+402 to the reference observation point PRij via the transmission focal point F, and a length of the path 403 from the reference observation point PRij to each reception transducer Rwk can be geometrically calculated. More specifically, regarding delay time with respect to the reference observation point PR, as illustrated in FIG. 17, the delay time calculator 10431 geometrically calculates length of paths from the reference observation point PR to each reception transducer Rwk (k=1 to kmax), based on information indicating position of the reception transducer Rw and information indicating position of the reference observation point PR, in correspondence with a transmission event. A difference Δdk of path length from the reference observation point PR to each reception transducer Rwk is divided by the sound velocity value Cs to calculate, for each reception transducer Rwk, a delay time Δtk of a reflected wave arriving at each reception transducer Rw from any reference observation point PR.

2. Application of Reference Delay Time to Dependent Observation Point PF

The delay-and-sum section 1043 pertaining to Embodiment 2 also generates an acoustic line signal by applying a reference delay time to each of the reception transducers Rw with respect to the reference observation point PR and one or more dependent observation points PF that are contiguous with the reference observation point PR in the depth direction. At this time, the reference delay time calculated for the reference observation point PR is applied to the dependent observation points PF that are contiguous with the reference observation point PR in the depth direction. Details of a method of applying reference delay time to dependent observation points PF are provided later.

<Operations>

Figure 18:
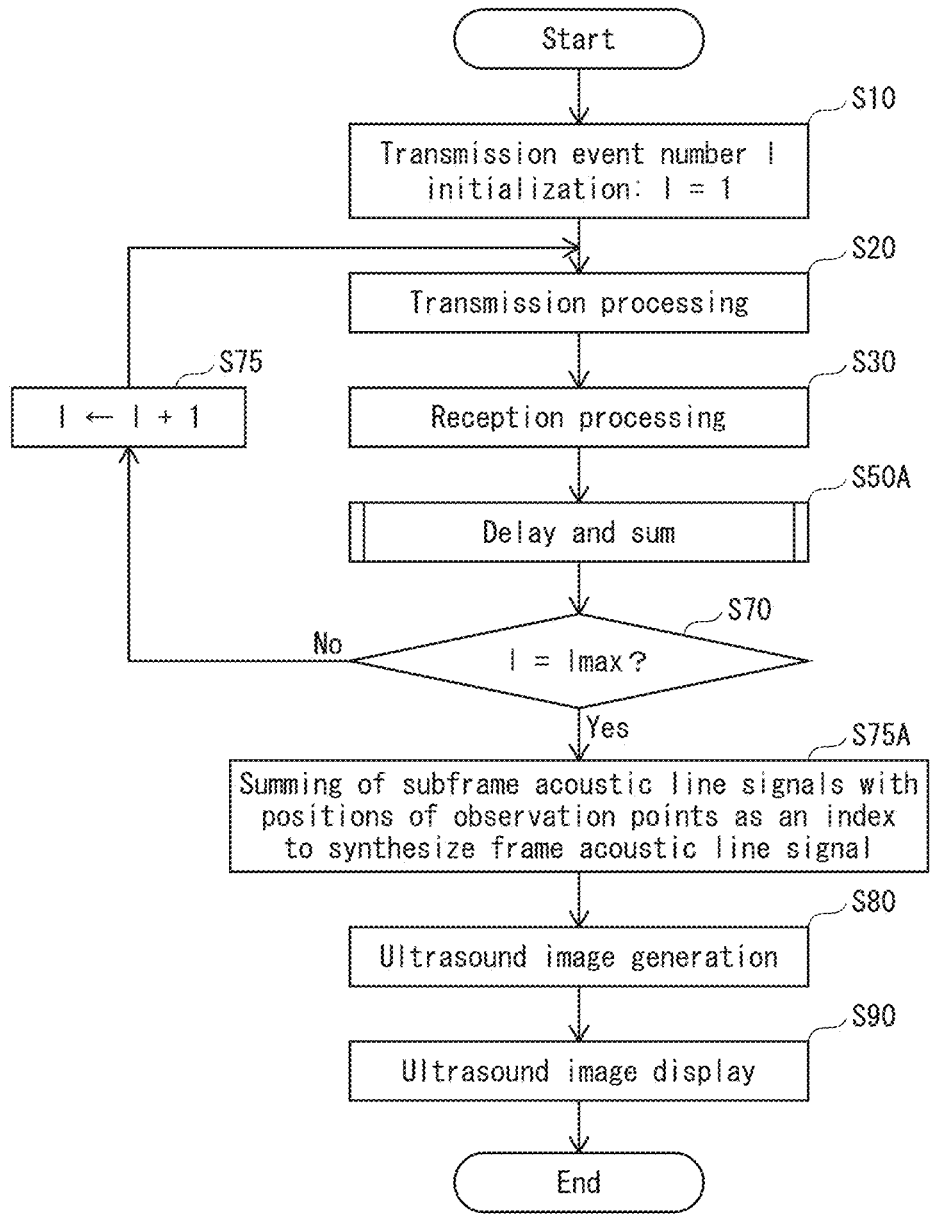
FIG. 18 is a flowchart illustrating processing in an ultrasound signal processing device pertaining to Embodiment 2.

The following is a description of operations of an ultrasound signal processing device pertaining to Embodiment 2, with reference to the drawings. FIG. 18 is a flowchart illustrating processing in an ultrasound signal processing device pertaining to Embodiment 2. Operations that are the same as in FIG. 12 are assigned the same step numbers, and description thereof is not repeated here.

First, an index 1 representing a transmission event number is initialized (step S10).

Next, in step S20, the transmitter 1031 performs transmission processing supplying a transmission signal for causing transmission of an ultrasound beam to each transducer included in a transmission aperture Tx (a transmission event).

Next, in step S30, the receiver 1041 generates reception signals based on reception of a reflected wave, and the reception signals are stored by the reception signal holding section 1042.

Next, in step S50A, the delay-and-sum section 1043 generates one frame of acoustic line signals with respect to all observation points in a region of interest in the subject for which an ultrasound image is to be generated.

Figure 19:
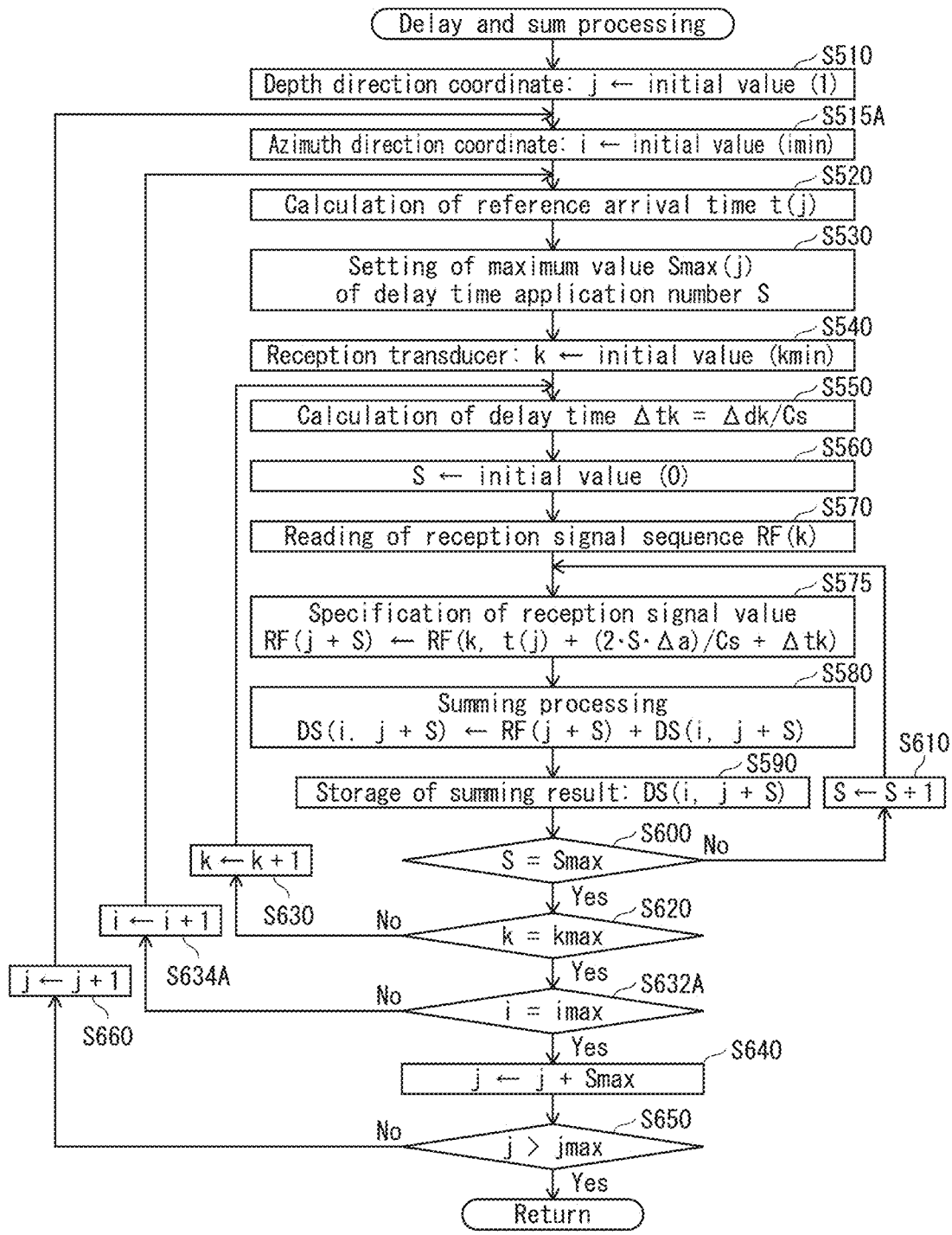
FIG. 19 is a flowchart illustrating details of delay-and-sum processing (step S50) in FIG. 18.
Figure 20:
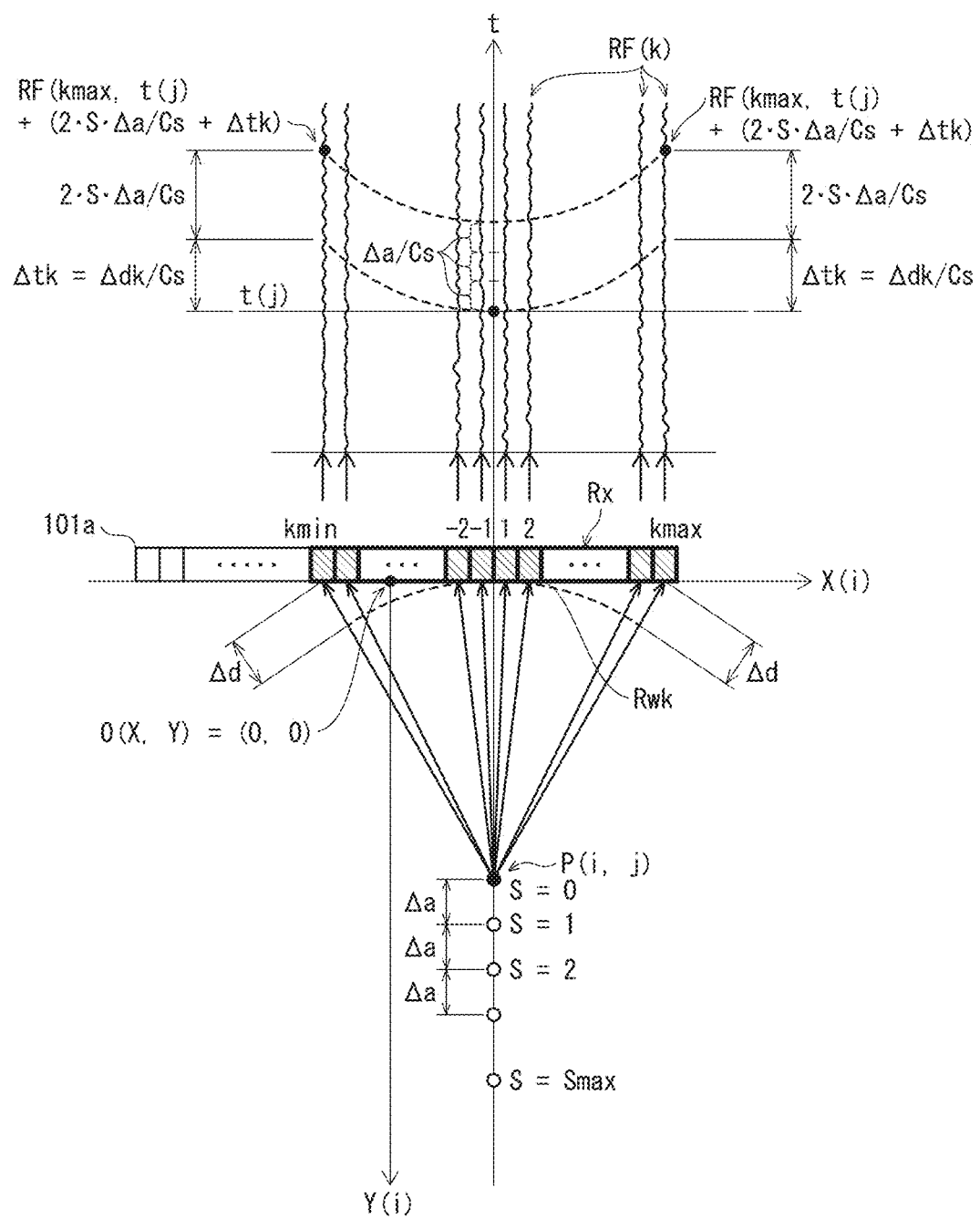
FIG. 20 is a schematic diagram for describing an operation of acoustic line signal generation regarding dependent observation points PF in delay-and-sum section 1043 pertaining to Embodiment 2.

The following describes details of processing in step S50A. FIG. 19 is a flowchart illustrating details of delay-and-sum processing (step S50A). FIG. 20 is a schematic diagram for describing an operation of acoustic line signal generation regarding dependent observation points PF in the delay-and-sum section 1043.

Operations that are the same as in FIG. 13 are assigned the same step numbers, and description thereof is not repeated here.

First, an index j representing the depth direction coordinate Y of the observation point P(i,j) is set to an initial value (1) (step S510), an index i representing the azimuth direction coordinate X of the observation point P(i,j) is set to an initial value (imin) (step S515A), and a reference delay time t(j) is calculated (step S520).

Next, a maximum value Smax(j) of a delay time application number S is set (step S530). An index k for identifying the reception transducers Rw is set to an initial value, and is here set to kmin, as one example (step S540).

Next, the delay time calculator 10431 calculates the delay time Δtk for arrival of a reflected wave from the observation point P(i,j) to the reception transducer Rwk. More specifically, as illustrated in FIG. 17, the delay time calculator 10431 geometrically calculates length of a path from the observation point P(i,j) to the reception transducer Rwk, based on information indicating position of the reception transducer Rwk and information indicating position of the observation point P(i,j), and calculates the delay time Δtk for arrival of a reflected wave to each reception transducer Rwk from the observation point P(i,j) by dividing a path length difference Δdk from the observation point P(i,j) to the reception transducers Rwk by the sound velocity value Cs.

Next, the delay processor 10433 sets the delay time application number S to an initial value (0) (step S560), reads a reception signal sequence RF(k) from the reception signal holding section 1042 (step S570), specifies a reception signal value RF(k,t(j)+Δtk) in the reception signal sequence RF(k), and sets it as a reception signal value RF(j+S) (step S575).

Next, the summer 10434 the reception signal value RF(j+S) is replaced by an acoustic line signal DS(j+S) (step S580), and the acoustic line signal DS(j+S) is stored in the summing register (step S590).

Then, whether or not the delay time application number S is the maximum value Smax is determined (step S600), and if not the maximum value Smax, S is incremented (step S610) and processing returns to step S575, where a reception signal value RF(k,t(j)+(2·S·Δa)/Cs+Δtk) is specified and set as a reception signal value RF(j+S), and a sum of the reception signal value RF(j+S) and an acoustic line signal DS(j+S) stored in the summing register (step S580) is stored in the summing register (step S590).

In step S600, if the delay time application number S is the maximum value Smax, whether or not the index k identifying a reception transducer Rw is the maximum value kmax is determined (step S620), and if not the maximum value kmax, k is incremented (step S630) and processing returns to step S550. In step S620, when k is the maximum value kmax of the reception transducers Rw in the reception aperture Rx, whether or not i the maximum value imax is determined (step S632A). When i is not the maximum value imax, i is incremented (step S634A), and processing returns to step S520. When i is the maximum value imax, an acoustic line signal DS(i,j+S) (i=1 to imax, S=0 to Smax) is calculated with respect to an observation point P (i,j+S) (S=0 to Smax), j is replaced by j+Smax (step S640), and whether or not j exceeds a maximum value jmax is determined (step S650). If j does not exceed the maximum value jmax, j is incremented (step S660) and processing returns to step S515A. If j exceeds the maximum value jmax, an acoustic line signal DS(i,j) (i=1 to imax, j=1 to jmax) is calculated, and processing returns to step S50A.

Next, returning to FIG. 18, whether or not the transmission event number 1 is equal to a maximum value lmax is determined (step S70), in order to judge whether or not ultrasound transmission is complete from all the transducers 101a of the probe 101. If not complete, 1 is incremented (step S75), processing returns to step S20, and a transmission event is performed with a gradual shift in the array direction of the transmission aperture Tx. If complete, processing proceeds to step S75A.

Next, in step S75A, the synthesizer 10435 sums a plurality of acoustic line signals DS(i,j) using position of observation points Pij for which acoustic line signals included in the acoustic line signals DS(i,j) are acquired as an index, thereby generating a synthesized acoustic line signal with respect to each observation point Pij.

Figure 21:
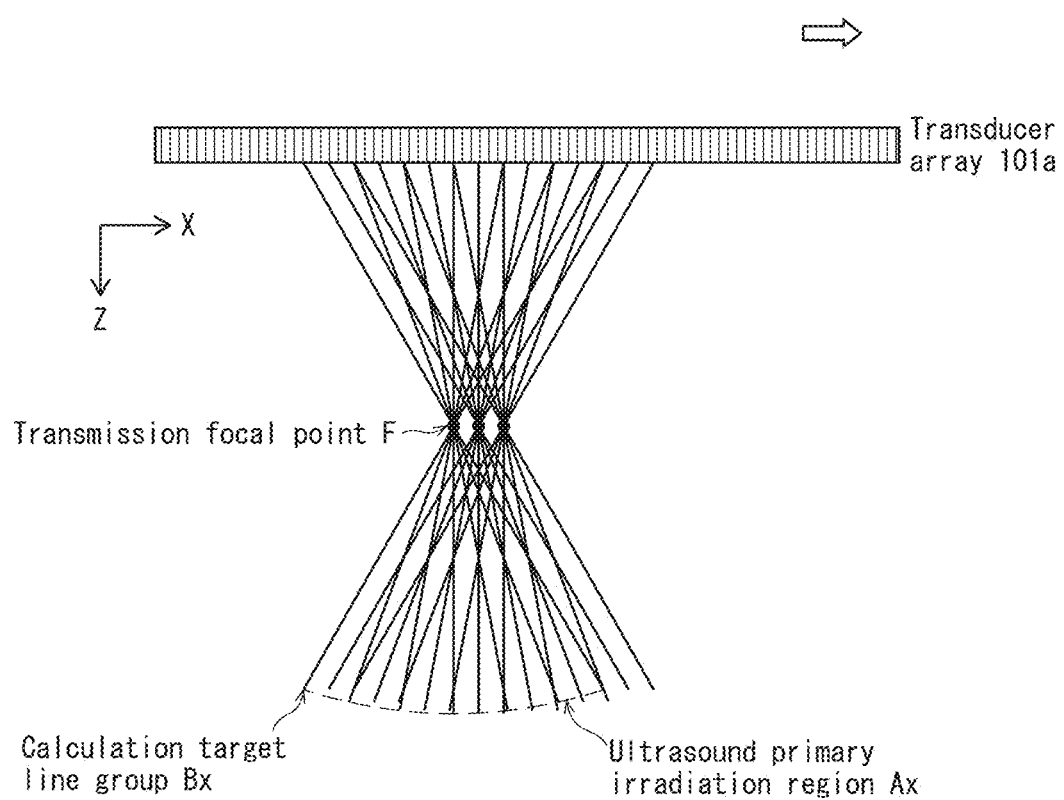
FIG. 21 is a schematic diagram illustrating synthesized acoustic line signal synthesis processing by a synthesizer 10435 pertaining to Embodiment 2.

FIG. 21 is a schematic diagram illustrating synthesized acoustic line signal synthesis processing by the synthesizer 10435. As described above, ultrasound transmission is sequentially performed by shifting the transducers used in the transmission transducer array (transmission aperture Tx) one transducer in the transducer array direction each time, in correspondence with transmission events. Thus, a position of the calculation target region Bx based on different transmission events also differs by one transducer in the same direction for each transmission event. By summing a plurality of acoustic line signals DS(i,j) with position of observation points Pij for which acoustic line signals were acquired as an index, one frame of acoustic line signals covering all of a region of interest is synthesized.

Further, regarding observation points Pij present across a plurality of calculation target regions Bx having different positions each transmission event, values of acoustic line signals DS(i,j) calculated for each transmission event are summed, and therefore a synthesized acoustic line signal indicates a larger value the greater the number of calculation target regions Bx corresponding to transmission events an observation point Pij is in. Here, a number of times an observation point Pij is included in a calculation target region Bx is defined as a "superposition number" and a maximum value of superposition in the transducer array direction is defined as a "maximum superposition number".

Next, in step S80, the ultrasound image generator 105 subjects one frame of acoustic line signals outputted from the delay-and-sum section 1043 to processing such as envelope detection, logarithmic compression, and the like to perform luminance conversion, and subjects a resulting luminance signal to coordinate transformation into an orthogonal coordinate system in order to generate an ultrasound image (B mode image) of one frame.

Next, in step S90, the display 106 displays on a display screen the ultrasound image of one frame outputted from the ultrasound image generator 105, and the ultrasound signal processing operation is complete.

<Brief Summary>

In the ultrasound signal processing device 150 pertaining to Embodiment 2 as described above, in addition to the structure described pertaining to Embodiment 1, the delay-and-sum section 1043 generates the acoustic line signals by performing delay-and-sum processing with respect to the reception signal sequences RFk based on reflected waves obtained from the ultrasound primary irradiation region Ax, with respect to observation points Pij corresponding to positions in the ultrasound primary irradiation region Ax.

According to this configuration, a simple calculation method can be implemented of applying the reference delay time to dependent observation points PFij even when delay-and-sum processing is performed with respect to a large number of dependent observation points PFij, and an acoustic line signal can be generated in one transmission event with respect to observation points distributed in an ultrasound primary irradiation region Ax.

According to at least one embodiment, the delay-and-sum section 1043, in the calculating of the ultrasound round-trip time between the dependent observation point PFij and the reception transducer Rwk nearest to the dependent observation point PFij, performs summing of the reference ultrasound round-trip time between the reference observation point PRij and the reception transducer Rwk nearest to the reference observation point PRij and an ultrasound round-trip time between the reference observation point PRij and the dependent observation point PFij.

According to this configuration, a simple calculation method can be implemented of applying the reference delay time to dependent observation points even when a synthetic aperture method should be applied to delay-and-sum processing with respect to a large number of observation points, and it is possible to specifically configure an ultrasound signal processing device capable of reducing calculation load of delay processing with respect to dependent observation points.

According to at least one embodiment, the transmitter 1031 repeatedly performs a transmission event of transmitting the ultrasound beam, and shifts the array of the transmission transducers Tx in the azimuth direction for each of the transmission events, and the ultrasound signal processing device 150 further comprises a synthesizer 10435 that generates a synthesized acoustic line signal by synthesizing a plurality of acoustic line signals DS by using positions of observation points Pij as a reference, based on reflected ultrasound received from the subject in correspondence with each of the transmission events.

According to this configuration, with respect to a synthetic aperture method of generating and synthesizing acoustic line signals with respect to an entire ultrasound primary irradiation region from one ultrasound transmission event by using convergent transmission beamforming, a calculation load for calculating delay time for each observation point can be reduced. As a result, calculation load for acoustic line signal generation can be reduced while suppressing a reduction in spatial resolution and signal to noise ratio.

At this time, in a range deeper than the focal point F in the depth direction in the region of interest, the greater the number of acoustic line signals DS superposed with respect to the same observation point Pij having the same position in the azimuth direction and the depth direction, the greater the number of the dependent observation points PFij with respect to the reference observation point PRij.

According to this configuration, the reduction in calculation load pertaining to delay time calculation with respect to observation points can be adjusted according to a number of superposed acoustic line signals DS.

<<Modification 1>>

According to at least one embodiment, a probe configuration is illustrated in which the transducers 101a are arranged along a one-dimensional direction. However, configuration of the probe 101 is not limited to this. For example, a two-dimensional transducer array in which the transducers 101a are arrayed on a two-dimensional plane or a rocking-type probe that acquires a three-dimensional tomographic image by mechanical rocking of a plurality of transducers arranged along a one-dimensional direction may be used as appropriate, depending on measurement requirements.

Figure 22:
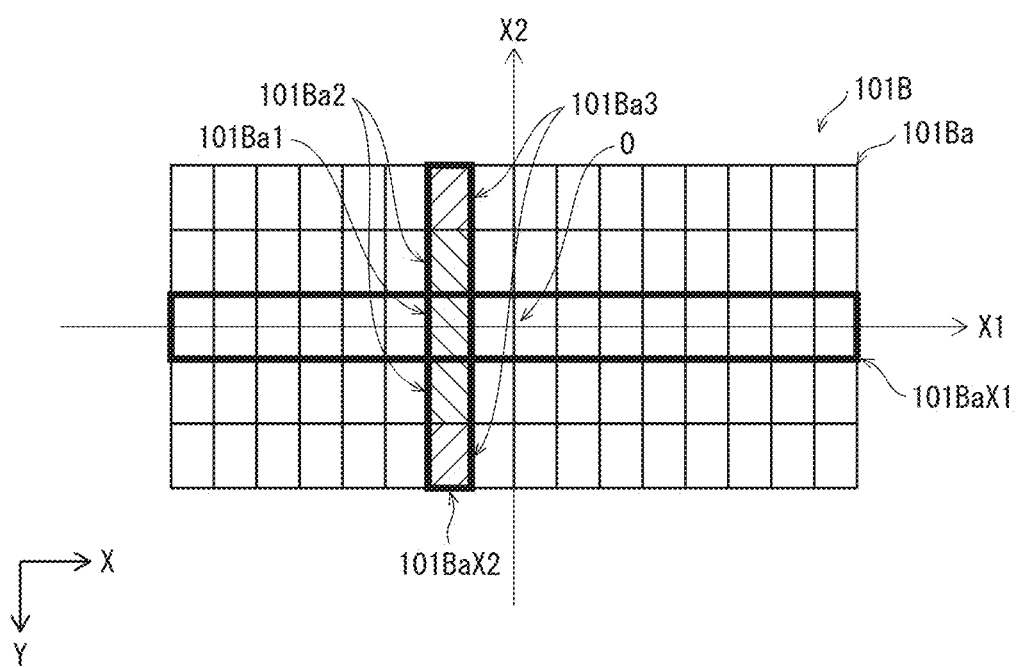
FIG. 22 is a schematic plan view diagram illustrating an aspect of transducers 101Ba of a probe 101B used in an ultrasound signal processing device pertaining to Modification 1.
Figure 23:
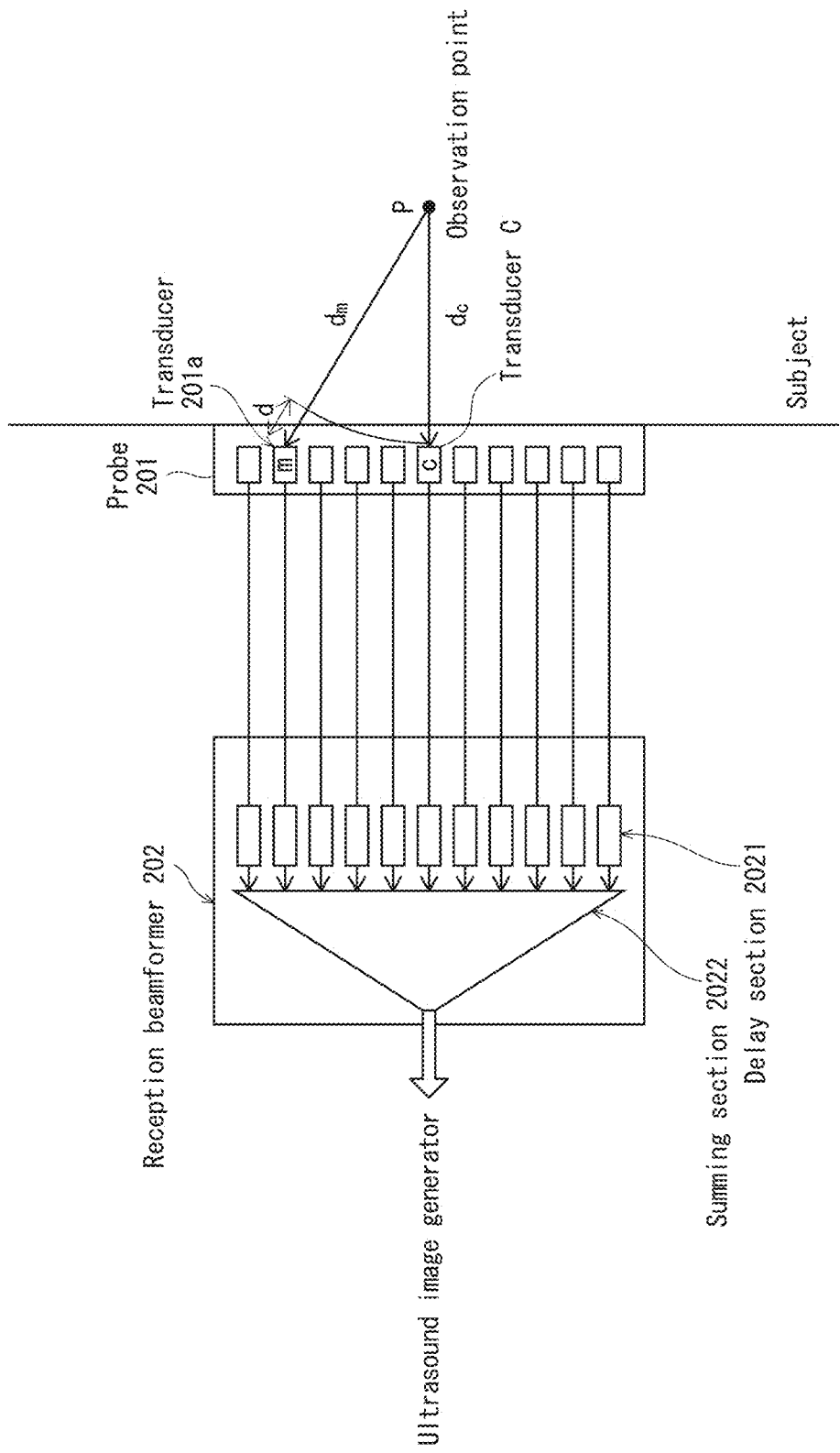
FIG. 23 is a schematic diagram for describing delay-and-sum processing in a conventional ultrasound signal processing device.
Figure 24B:
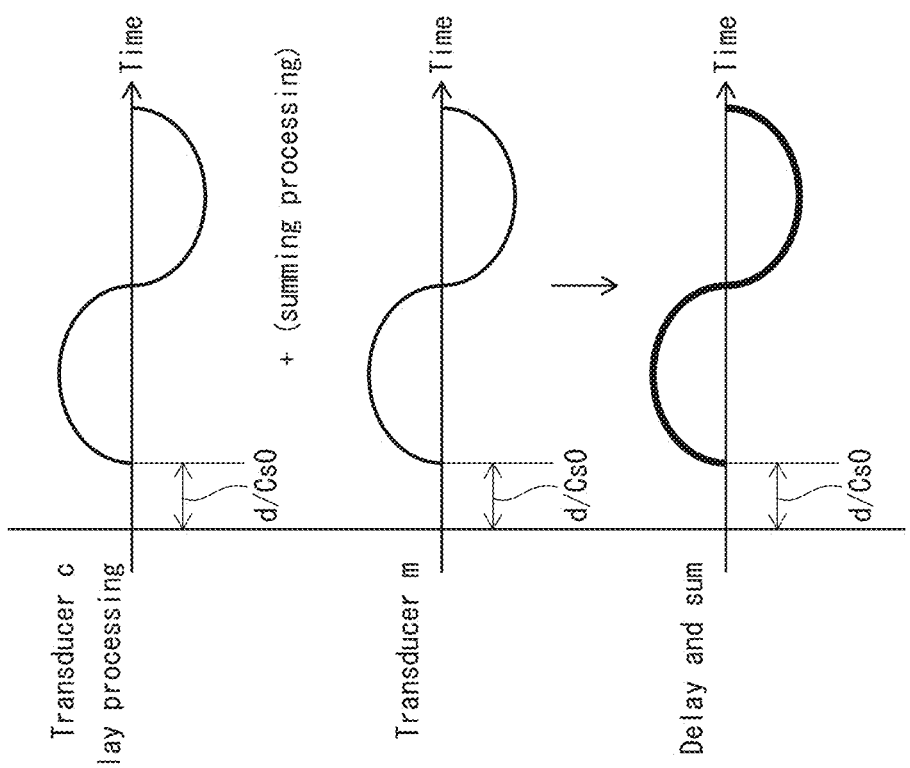
FIGS. 24A and 24B are schematic diagrams for describing influence of acoustic velocity changes on delay-and-sum processing in a conventional ultrasound signal processing device.
Figure 24A:
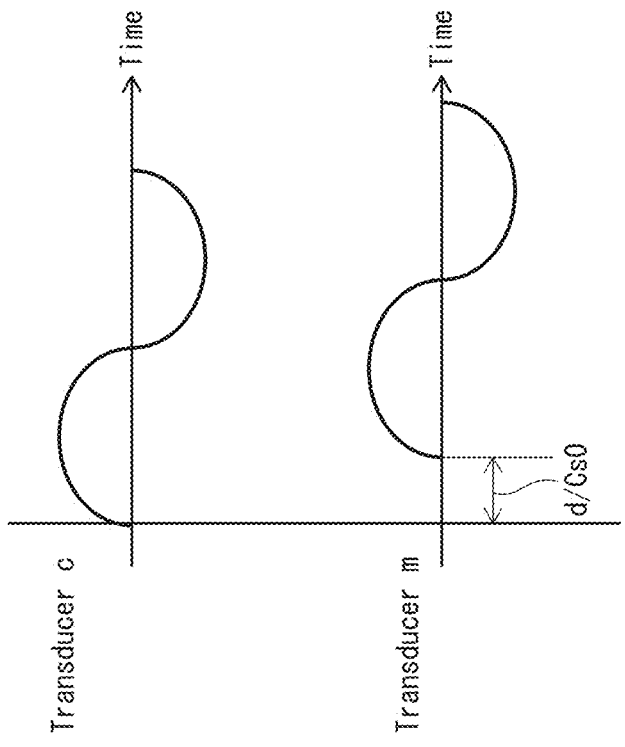

FIG. 22 is a schematic plan view diagram illustrating an aspect of transducers 101Ba of a probe 101B used in an ultrasound signal processing device pertaining to Modification 1. In the probe 101B, the transducers 101Ba are arranged in two dimensions (X1, X2), and by individually changing timing of voltage application and voltage values applied to the transducers 101Ba, it is possible to control irradiation position and direction of a transmitted ultrasound beam in three dimensions (X1, X2, Y).

According to the ultrasound signal processing device pertaining to Modification 1, beamforming in an X1 direction uses a one-dimensional transducer array 101BaX1 positioned centrally in an X2 direction to perform processing that is the same as for the transmission beamformer 103 and the reception beamformer 104 described for Embodiment 1 or Embodiment 2.

On the other hand, beamforming in the X2 direction employs a configuration in which a simple process is applied to delay time calculated based on transmission and reception from the transducer array 101BaX1 positioned centrally in the X2 direction.

More specifically, for example, the delay time $\Delta tk$ that is calculated as if transducers 101Ba1 that are central in the X2 direction are the reception transducers Rwk is applied to transducers 101Ba2 that are adjacent to the transducers 101Ba1; and regarding transducers 101Ba3 that are positioned on the outside in the X2 direction, processing that is the same as for transmission beamformer 103 and the reception beamformer 104 described for Embodiment 1 or Embodiment 2 is performed by using a one-dimensional transducer array in the X1 direction positioned on the outside in the X2 direction. According to this configuration, the calculation load for delay-and-sum processing can be reduced to ⅔.

Alternatively, the delay time $\Delta tk$ calculated treating the transducers 101Ba1 as reception transducers Rwk may also be applied to the transducers 101Ba3 positioned on the outside in the X2 direction. Alternatively, a delay time $\Delta tk$ that is longer than the delay time $\Delta tk$ applied to the transducers 101Ba1 by a certain time may be applied. In this case, the calculation load of delay-and-sum processing can be reduced to ⅕.

As described above, according to a configuration pertaining to Modification 1, in beamforming in a direction orthogonal to an azimuth direction of a two-dimensional probe, simple processing can be adopted such that a delay time calculated based on transmission and reception from a transducer array 101BaX1 positioned centrally in the azimuth direction can also be applied to the transducers 101B2 and the transducers 101Ba3, and therefore even when using a two-dimensional probe for which calculation load is relatively large, the calculation load of delay-and-sum processing can be reduced.

<<Modification 2>>

According to the ultrasound diagnostic device 100 pertaining to at least one embodiment, the delay-and-sum section 1043, with respect to a reference observation point PRij selected from observation points in a region of interest corresponding to an analysis target range of a subject, calculates a delay time of arrival of a reflected wave from the reference observation point PRij to each reception transducer Rwk as a reference delay time $\Delta tk$ and generates acoustic line signals DS by using the reference delay time $\Delta tk$ for each reception transducer Rwk. Further, with respect to one or more dependent observation points PFij that are contiguous in the depth direction from the reference observation point PRij, the delay-and-sum section 1043 generates acoustic line signals DS by using the reference delay time $\Delta tk$ with respect to each of the reception transducers Rwk.

However, according to an ultrasound signal processing device pertaining to Modification 2, the reference observation point is set as a first reference observation point PRij, and a second reference observation point PRij that is contiguous with the first reference observation point PRij in the depth direction is selected, and a delay time of arrival of a reflected wave from the second reference observation point PRij to each reception transducer Rwk is calculated as a second reference delay time $\Delta tk$, and acoustic line signals DS are generated for each reception transducer Rwk by using the second reference delay time $\Delta tk$. Further, with respect to one or more dependent observation points PFij that are contiguous in the depth direction from the first and second reference observation points PRij, acoustic line signals DS are generated by application of an interpolated delay time $\Delta tk$ calculated by interpolation based on the first reference delay time $\Delta tk$ and the second reference delay time $\Delta tk$.

In this case, according to the ultrasound signal processing device pertaining to Modification 2, immediately after an iteration calculating the first reference delay time $\Delta tk$ with respect to the first reference observation point PRij, an iteration is performed calculating the second reference delay time $\Delta tk$ with respect to the second reference observation point PRij, and therefore calculation of the first and second reference delay time with respect to both reference observation points PRij can be performed before delay-and-sum processing with respect to a dependent observation point PFij. Thus, the interpolated delay time used in delay-and-sum processing with respect to the dependent observation point PFij can be calculated appropriately.

Further, calculation of the interpolated delay time, with respect to a dependent observation point PFij, the first reference delay time and the second reference delay time $\Delta tk$, can be performed by interpolation based on a distance between a dependent observation point PFij and the first reference observation point PRij or the second reference observation point PRij. Then acoustic line signals can be generated by applying the interpolated delay time to each reception transducer with respect to dependent observation points PRij. According to this configuration, even when a region of interest is positioned where a refractive index of tissue of the subject rapidly changes, a more accurate interpolated delay time can be applied to delay-and-sum processing with respect to a dependent observation point PFij.

As described above, according to an ultrasound signal processing device and an ultrasound signal processing method pertaining to aspects of the present disclosure, it is possible to reduce a calculation load of delay time calculation processing, which is a relatively large portion of delay-and-sum processing, thereby reducing an overall calculation load of the delay-and-sum processing, while suppressing a decrease in spatial resolution and signal to noise ratio of acoustic line signals.

<<Other Modifications>>

In the ultrasound diagnostic device 100 pertaining to at least one embodiment, configuration of the transmission beamformer 103 and the reception beamformer 104 can be changed as appropriate.

For example, according to at least one embodiment, the transmitter 1031 sets a transmission aperture Tx that is an array of transmission transducers corresponding to a plurality of the transducers 101a of the probe 101, and repeats ultrasound transmission while gradually shifting the transmission aperture Tx in the array direction with each ultrasound transmission in order to perform ultrasound transmission from all of the transducers 101a of the probe 101.

However, the transmitter 1031 may be configured to perform ultrasound transmission from all of the transducers 101a of the probe 101. Without repeating ultrasound transmission, reflected ultrasound can be received from an entirety of the ultrasound primary irradiation region Ax from one ultrasound transmission.

Further, according to at least one embodiment, the calculation target region Bx is a straight line region having a width of one transducer, perpendicular to the transducer array and passing through an array center of the reception aperture Rx.

However, the calculation target region Bx is not limited to this example, and may be set as any region included in the ultrasound primary irradiation region Ax. For example, a rectangular region having a width of a plurality of transducers, extending in a straight line perpendicular to the transducer array and passing through an array center of the reception aperture Rx may be used. Further, an hourglass-shaped region similar to the ultrasound primary irradiation region Ax may be used. Further, the calculation target regions Bx set for each transmission event may be set to overlap in the transducer array direction. It is possible to improve the signal to noise ratio of ultrasound images generated by synthesizing acoustic line signals of regions that overlap, according to a synthetic aperture method.

Further, the present disclosure describes the embodiments above, but the present disclosure is not limited to these embodiments, and the following examples are also included in the scope of the present invention.

For example, the present invention may be a computer system including a microprocessor and a memory, the memory storing a computer program and the microprocessor operating according to the computer program. For example, the present invention may be a computer system that operates (or instructs operation of connected elements) according to a computer program of a diagnostic method of an ultrasound diagnostic device of the present invention.

Further, examples in which all or part of the ultrasound diagnostic device, or all or part of a beamforming section are constituted by a computer system including a microprocessor, a storage medium such as ROM, RAM, etc., a hard disk unit, and the like, are included in the present invention. A computer program for achieving the same operations as the devices described above may be stored in RAM or a hard disk unit; the microprocessor operating according to the computer program, thereby realizing the functions of each device.

Further, all or part of the elements of each device may be configured as one system large scale integration (LSI). A system LSI is an ultra-multifunctional LSI manufactured by integrating a plurality of elements on one chip, and more specifically is a computer system including a microprocessor, ROM, RAM, and the like. The plurality of elements can be integrated on one chip, or a portion may be integrated on one chip. Here, LSI may refer to an integrated circuit, a system LSI, a super LSI, or an ultra LSI, depending on the level of integration. A computer program for achieving the same operation as the devices described above may be stored in the RAM; the microprocessor operating according to the computer program, the system LSI thereby realizing the functions of each device. For example, a case of the beamforming method of the present invention stored as a program of an LSI, the LSI being inserted into a computer and a defined program (beamforming method) being executed is also included in the present invention.

Note that methods of circuit integration are not limited to LSI, and implementation may be achieved by a dedicated circuit or general-purpose processor. After LSI manufacture, a field programmable gate array (FPGA) or a reconfigurable processor, in which circuit cell connections and settings in the LSI can be reconfigured, may be used.

Further, if a circuit integration technology is introduced that replaces LSI due to advances in semiconductor technology or another derivative technology, such technology may of course be used to integrate the function blocks.

Further, all or part of the functions of an ultrasonic diagnostic device pertaining to at least one embodiment may be implemented by execution of a program by a processor such as a CPU. The present invention may be a non-transitory computer-readable storage medium on which a program is stored that causes execution of an MTI filter or velocity analysis of an ultrasound diagnostic device described above. A program and signals may be recorded and transferred on a storage medium so that the program may be executed by another independent computer system, or the program may of course be distributed via a transmission medium such as the Internet.

Alternatively, each component element of an ultrasound diagnostic device pertaining to an embodiment may be implemented by a programmable device such as a central processing unit (CPU), a graphics processing unit (GPU), a processor, or the like, and software. A configuration using a GPU may be referred to as general-purpose computing on a graphics processing unit (GPGPU). These component elements can each be a single circuit component or an assembly of circuit components. Further, a plurality of component elements can be combined into a single circuit component or can be an aggregate of a plurality of circuit components.

According to an ultrasound diagnostic device pertaining to at least one embodiment, the ultrasound diagnostic device includes a data storage as a storage device. However, the storage device is not limited to this example and may be a semiconductor memory, hard disk drive, optical disk drive, magnetic storage device, or the like that is externally connectable to the ultrasound diagnostic device.

Further, the division of function blocks in the block diagrams is merely an example, and a plurality of function blocks may be implemented as one function block, one function block may be divided into a plurality, and a portion of a function may be transferred to another function block. Further, a single hardware or software element may process the functions of a plurality of function blocks having similar functions in parallel or by time division.

Further, the order in which steps described above are executed is for illustrative purposes, and the steps may be in an order other than described above. Further, a portion of the steps described above may be executed simultaneously (in parallel) with another step.

Further, the ultrasound diagnostic device is described as having an externally connected probe and display, but may be configured with an integral probe and/or display.

Further, a portion of functions of transmitters and receivers may be included in the probe. For example, a transmission electrical signal may be generated and converted to ultrasound in the probe, based on a control signal for generating a transmission electrical signal outputted from the transmitter. It is possible to use a configuration that converts received reflected ultrasound into a reception electrical signal and generates a reception signal based on the reception electrical signal in the probe.

Further, at least a portion of functions of each ultrasound diagnostic device pertaining to an embodiment, and each modification thereof, may be combined. Further, the numbers used above are all illustrative, for the purpose of explaining the present invention in detail, and the present invention is not limited to the example numbers used above.

Further, the present invention includes various modifications that are within the scope of conceivable ideas by a person skilled in the art.

<<Review>>

The ultrasound signal processing device pertaining to at least one embodiment is an ultrasound signal processing device that transmits an ultrasound beam into a subject by using an ultrasound probe in which transducers are arranged along an azimuth direction and generates acoustic line signals based on reflected waves obtained from the subject, the ultrasound signal processing device comprising: ultrasound signal processing circuitry, the ultrasound signal processing circuitry comprising: a transmitter that causes an array of transmission transducers selected from the transducers to transmit the ultrasound beam; a receiver that, based on reflected waves received by an array of reception transducers selected from the transducers, generates reception signal sequences corresponding to the reception transducers; and a delay-and-sum section that, for a reference observation point selected from observation points in a region of interest corresponding to an analysis target range of the subject, (i) calculates delay times of reflected wave arrival to each of the reception transducers from the reference observation point as reference delay times, and (ii) generates acoustic line signals by using the reference delay times corresponding to the reception transducers, and for one or more dependent observation points in the region of interest that are contiguous in a depth direction from the reference observation point, (iii) generates acoustic line signals by applying the reference delay times corresponding to the reception transducers.

According to this configuration, it is possible to reduce a calculation load of delay time calculation processing, which is a relatively large portion of delay-and-sum processing, thereby reducing an overall calculation load of the delay-and-sum processing, while suppressing a decrease in spatial resolution and signal to noise ratio of frame acoustic line signals.

According to at least one embodiment, the delay-and-sum section generates the acoustic line signals with respect to the reference observation point by specifying reception signal values corresponding to the reference delay times corresponding to the reception transducers from reception signal sequences corresponding to the reception transducers, and performing summing with respect to the reception transducers, and the delay-and-sum section generates the acoustic line signals with respect to the one or more dependent observation points by specifying reception signal values corresponding to the reference delay times corresponding to the reception transducers from reception signal sequences corresponding to the reception transducers, and performing summing with respect to the reception transducers.

According to this configuration, it is possible to reduce a calculation load required for delay time calculation with respect to a dependent observation point.

According to at least one embodiment, the delay-and-sum section generates the acoustic line signals with respect to the reference observation point by calculating a reference ultrasound round-trip time between the reference observation point and a reception transducer nearest to the reference observation point, calculating reflected wave arrival times that are each a sum of the reference ultrasound round-trip time and the reference delay time corresponding to the reception transducer, specifying reception signal values obtained from the reflected wave arrival times from reception signal sequences corresponding to the reception transducers, and performing summing with respect to the reception transducers, and the delay-and-sum section generates the acoustic line signals with respect to each of the one or more dependent observation points by calculating an ultrasound round-trip time between the dependent observation point and a reception transducer nearest to the dependent observation point, calculating approximate reflected wave arrival times that are each a sum of the reference ultrasound round-trip time and the reference delay time corresponding to the reception transducer, specifying reception signal values obtained from the approximate reflected wave arrival time from reception signal sequences corresponding to the reception transducers, and performing summing with respect to the reception transducers.

According to this configuration, it is possible to realize a simple calculation method of applying a reference delay time to delay times of dependent observation points, and to configure an ultrasound signal processing device that can reduce a calculation load of delay processing with respect to the dependent observation points.

According to at least one embodiment, the delay-and-sum section, in the calculating of the ultrasound round-trip time between the dependent observation point and the reception transducer nearest to the dependent observation point, performs summing of the ultrasound round-trip time between the reference observation point and the reception transducer nearest to the reference observation point and an ultrasound round-trip time between the reference observation point and the dependent observation point.

According to this configuration, a simple calculation method can be implemented of applying the reference delay time to dependent observation points even when a synthetic aperture method should be applied to delay-and-sum processing with respect to a large number of observation points, and it is possible to specifically configure an ultrasound signal processing device capable of reducing calculation load of delay processing with respect to dependent observation points.

According to at least one embodiment, the greater the depth in the subject, the greater the number of the dependent observation points with respect to the reference observation point.

According to this configuration, for example, as depth increases, a sampling period increases in steps to reduce reference observation point occurrence frequency, thereby making it possible to prevent the inefficiency of calculation results not being reflected in output even when delay processing calculation is performed with respect to each observation point adjacent in the depth direction, and delay processing calculation results can be reflected in the output without excess or shortfall.

According to at least one embodiment, in the region of interest, a plurality of sets of the reference observation point and the one or more dependent observation points alternate in the depth direction of the subject.

According to at least one embodiment, the transmitter sets a focal point defining a point which the ultrasound beam converges towards in the subject, and causes the transmission to be performed such that the ultrasound beam converges towards the focal point from the array of the transmission transducers in an ultrasound primary irradiation region defined as a range between two straight lines that cross at the focal point and connect to transducers at ends of the array of the transmission transducers. Further, according to at least one embodiment, the delay-and-sum section generates the acoustic line signals by performing delay-and-sum processing with respect to the reception signal sequences based on reflected waves obtained from the ultrasound primary irradiation region, with respect to observation points positioned on a line parallel to the depth direction passing through the focal point among observation points corresponding to positions in the ultrasound primary irradiation region.

Further, according to at least one embodiment, the delay-and-sum section generates the acoustic line signals by performing delay-and-sum processing with respect to the reception signal sequences based on reflected waves obtained from the ultrasound primary irradiation region, with respect to observation points corresponding to positions in the ultrasound primary irradiation region.

According to this configuration, a simple calculation method can be implemented of applying the reference delay time to dependent observation points even when delay-and-sum processing is performed with respect to a large number of dependent observation points, and an acoustic line signal can be generated in one transmission event with respect to observation points distributed in an ultrasound primary irradiation region Ax.

According to at least one embodiment, the transmitter repeatedly performs a transmission event of transmitting the ultrasound beam, and shifts the array of the transmission transducers in the azimuth direction for each of the transmission events, and the ultrasound signal processing device further comprises a synthesizer that generates a synthesized acoustic line signal by synthesizing a plurality of acoustic line signals by using positions of observation points as a reference, based on reflected ultrasound received from the subject in correspondence with each of the transmission events.

According to this configuration, with respect to a synthetic aperture method of generating and synthesizing acoustic line signals with respect to an entire ultrasound primary irradiation region from one ultrasound transmission event by using convergent transmission beamforming, a calculation load for calculating delay time for each observation point can be reduced. As a result, calculation load for acoustic line signal generation can be reduced while suppressing a reduction in spatial resolution and signal to noise ratio.

According to at least one embodiment, in a range deeper than the focal point in the depth direction in the region of interest, the greater the number of acoustic line signals superposed with respect to the same observation point having the same position in the azimuth direction and the depth direction, the greater the number of the dependent observation points with respect to the reference observation point.

According to this configuration, the reduction in calculation load pertaining to delay time calculation with respect to observation points can be adjusted according to a number of superposed acoustic line signals DS.

According to at least one embodiment, when an array of transducers arranged along the azimuth direction is a first transducer array, a plurality of second transducer arrays parallel to the first transducer array are arranged sandwiching the first transducer array, and the delay-and-sum section, when generating acoustic line signals with respect to the same observation point having the same position in the azimuth direction and the depth direction, (i) applies the reflected wave arrival times corresponding to the first transducer array to the second transducer arrays that are nearest to the first transducer array among the plurality of the second transducer arrays, and (ii) applies reflected wave arrival times longer than the reflected wave arrival times corresponding to first transducer array to the second transducer arrays farther from the first transducer array than the second transducer arrays that are nearest to the first transducer array.

According to this configuration, regarding beamforming in a direction perpendicular to the azimuth direction of a two-dimensional probe, a configuration is adopted that performs simple processing applying a delay time calculated based on transmission and reception from a transducer array positioned centrally in the azimuth direction to a transducer positioned towards an end of the array in the azimuth direction, and therefore a calculation load of delay-and-sum processing can be reduced even when using a two-dimensional probe for which the calculation load is relatively high.

According to at least one embodiment, when the reference observation point is a first reference observation point, the delay-and-sum section further selects a second reference observation point contiguous in the depth direction from the first reference observation point, calculates delay times of reflected wave arrival to each of the reception transducers from the second reference observation point as second reference delay times, and generates acoustic line signals by using the second reference delay times corresponding to the reception transducers, and with respect to each of the one or more dependent observation points, calculates interpolated delay times by interpolation of the reference delay times and the second reference delay times based on a distance between the dependent observation point and the first reference observation point or the second reference observation point, and with respect to each of the one or more dependent observation points, generates the acoustic line signals by applying the interpolated delay times corresponding to the reception transducers.

According to this configuration, even when a region of interest is positioned where a refractive index of tissue of the subject rapidly changes, a more accurate interpolated delay time can be applied to delay-and-sum processing with respect to a dependent observation point PFij.

According to at least one embodiment, the number of transducers included in the array of the transmission transducers increases as depth in the subject increases, in a range corresponding to a defined distance from a surface of the subject in the region of interest.

According to this configuration, it is possible to cut down on processing for a region in which spatial resolution and signal to noise ratio are low and reflected wave utilization efficiency is low, thereby suppressing execution of wasteful calculation with a low contribution to image quality improvement, enabling efficient use of calculation resources.

According to at least one embodiment, in the generating of the acoustic line signals with respect to the one or more dependent observation points, the delay times of reflected wave arrival to each of the reception transducers from the one or more dependent observation points are not calculated. Further, according to at least one embodiment, an ultrasound round-trip time between two points is a time obtained by dividing a round-trip distance between two points by a sound velocity value.

An ultrasound signal processing method pertaining to at least one embodiment is an ultrasound signal processing method of transmitting an ultrasound beam into a subject by using an ultrasound probe in which transducers are arranged along an azimuth direction and generating acoustic line signals based on reflected waves obtained from the subject, the ultrasound signal processing method comprising: causing an array of transmission transducers selected from the transducers to transmit the ultrasound beam; based on reflected waves received by an array of reception transducers selected from the transducers, generating reception signal sequences corresponding to the reception transducers; and for a reference observation point selected from observation points in a region of interest corresponding to an analysis target range of the subject, (i) calculating delay times of reflected wave arrival to each of the reception transducers from the reference observation point as reference delay times, and (ii) generating acoustic line signals by using the reference delay times corresponding to the reception transducers, and for one or more dependent observation points in the region of interest that are contiguous in a depth direction from the reference observation point, (iii) generating acoustic line signals by applying the reference delay times corresponding to the reception transducers.

According to at least one embodiment, the generating of the acoustic line signals with respect to the reference observation point is performed by calculating ultrasound round-trip time between the reference observation point and a reception transducer nearest to the reference observation point, calculating reflected wave arrival times that are each a sum of the ultrasound round-trip time and the reference delay time corresponding to the reception transducer, specifying reception signal values obtained from the reflected wave arrival times from reception signal sequences corresponding to the reception transducers, and performing summing with respect to the reception transducers, and the generating of the acoustic line signals with respect to each of the one or more dependent observation points is performed by calculating ultrasound round-trip time between the dependent observation point and a reception transducer nearest to the dependent observation point, calculating approximate reflected wave arrival times that are each a sum of the ultrasound round-trip time and the reference delay time corresponding to the reception transducer, specifying reception signal values obtained from the approximate reflected wave arrival time from reception signal sequences corresponding to the reception transducers, and performing summing with respect to the reception transducers.

According to this configuration, it is possible to realize a simple calculation method of applying a reference delay time to delay times of dependent observation points, and to realize ultrasound signal processing that can reduce a calculation load of delay processing with respect to the dependent observation points.

<<Supplement>>

Embodiments described above illustrate beneficial specific examples of the present invention. Numerical values, shapes, materials, constituent elements, positions and connections of constituent elements, processes, order of processes, and the like illustrated in embodiments are merely examples and are not intended to limit the present invention. Further, among constituent elements of embodiments, constituent elements not described in independent claims representing top level concepts of the present invention are described as constituent elements of a more beneficial form.

Further, in order to facilitate understanding of the invention, constituent elements of each drawing referenced in the description of an embodiment may be drawn not to scale. Further, the present invention is not limited by the description of any embodiment above, and can be appropriately changed without departing from the spirit of the present invention.

Further, members such as circuit components, lead wires and the like on a substrate are present in the ultrasound diagnostic device, but various aspects of the present invention can be realized based on ordinary knowledge in the technical fields concerning electrical wiring and electrical circuits, and therefore description of such members is not directly relevant to description of the present invention, and has been omitted. Note that each of the drawings described above is a schematic diagram, and is not necessarily a precise representation.

Although the technology pertaining to the present disclosure has been fully described by way of examples with reference to the accompanying drawings, various changes and modifications will be apparent to those skilled in the art. Therefore, unless such changes and modifications depart from the scope of the present disclosure, they should be construed as being included therein.

What is claimed is:

1. An ultrasound signal processing device that transmits an ultrasound beam into a subject by using an ultrasound probe in which transducers are arranged along an azimuth direction and generates acoustic line signals based on reflected waves obtained from the subject, the ultrasound signal processing device comprising:
   ultrasound signal processing circuitry, the ultrasound signal processing circuitry comprising:
   a transmitter that causes an array of transmission transducers selected from the transducers to transmit the ultrasound beam;
   a receiver that, based on reflected waves received by an array of reception transducers selected from the transducers, generates reception signal sequences corresponding to the reception transducers; and
   a delay-and-sum section that,
   for a reference observation point selected from observation points in a region of interest corresponding to an analysis target range of the subject, (i) calculates delay times of reflected wave arrival to each of the reception transducers from the reference observation point as reference delay times, and (ii) generates acoustic line signals by using the reference delay times corresponding to the reception transducers, and for one or more dependent observation points in the region of interest that are contiguous in a depth direction from the reference observation point, (iii) generates acoustic line signals by applying the reference delay times corresponding to the reception transducers, wherein the delay times applied for the one or more dependent observation points are the same as the delay times applied for the reference observation point, and wherein the number of dependent observation points PF to which the reference delay time of one reference observation point PR is applied is minimum for a closest of the reference observation points to the array of reception transducers and is maximum for a furthest of the reference observation points from the array of reception transducers.

2. The ultrasound signal processing device of claim 1, wherein the delay-and-sum section generates the acoustic line signals with respect to the reference observation point by specifying reception signal values corresponding to the reference delay times corresponding to the reception transducers from reception signal sequences corresponding to the reception transducers, and performing summing with respect to the reception transducers, and the delay-and-sum section generates the acoustic line signals with respect to the one or more dependent observation points by specifying reception signal values corresponding to the reference delay times corresponding to the reception transducers from reception signal sequences corresponding to the reception transducers, and performing summing with respect to the reception transducers.

3. The ultrasound signal processing device of claim 1, wherein the delay-and-sum section generates the acoustic line signals with respect to the reference observation point by calculating a reference ultrasound round-trip time between the reference observation point and a reception transducer nearest to the reference observation point, calculating reflected wave arrival times that are each a sum of the reference ultrasound round-trip time and the reference delay time corresponding to the reception transducer, specifying reception signal values obtained from the reflected wave arrival times from reception signal sequences corresponding to the reception transducers, and performing summing with respect to the reception transducers, and the delay-and-sum section generates the acoustic line signals with respect to each of the one or more dependent observation points by calculating an ultrasound round-trip time between the dependent observation point and a reception transducer nearest to the dependent observation point, calculating approximate reflected wave arrival times that are each a sum of the reference ultrasound round-trip time and the reference delay time corresponding to the reception transducer, specifying reception signal values obtained from the approximate reflected wave arrival time from reception signal sequences corresponding to the reception transducers, and performing summing with respect to the reception transducers.

4. The ultrasound signal processing device of claim 3, wherein the delay-and-sum section, in the calculating of the ultrasound round-trip time between the dependent observation point and the reception transducer nearest to the dependent observation point, performs summing of the reference ultrasound round-trip time between the reference observation point and the reception transducer nearest to the reference observation point and an ultrasound round-trip time between the reference observation point and the dependent observation point.

5. The ultrasound signal processing device of claim 1, wherein the greater the depth in the subject, the greater the number of the dependent observation points with respect to the reference observation point.

6. The ultrasound signal processing device of claim 1, wherein in the region of interest, a plurality of sets of the reference observation point and the one or more dependent observation points alternate in the depth direction of the subject.

7. The ultrasound signal processing device of claim 1, wherein the transmitter sets a focal point defining a point which the ultrasound beam converges towards in the subject, and causes the transmission to be performed such that the ultrasound beam converges towards the focal point from the array of the transmission transducers in an ultrasound primary irradiation region defined as a range between two straight lines that cross at the focal point and connect to transducers at ends of the array of the transmission transducers.

8. The ultrasound signal processing device of claim 7, wherein the delay-and-sum section generates the acoustic line signals by performing delay-and-sum processing with respect to the reception signal sequences based on reflected waves obtained from the ultrasound primary irradiation region, with respect to observation points positioned on a line parallel to the depth direction passing through the focal point among observation points corresponding to positions in the ultrasound primary irradiation region.

9. The ultrasound signal processing device of claim 7, wherein the delay-and-sum section generates the acoustic line signals by performing delay-and-sum processing with respect to the reception signal sequences based on reflected waves obtained from the ultrasound primary irradiation region, with respect to observation points corresponding to positions in the ultrasound primary irradiation region.

10. The ultrasound signal processing device of claim 8, wherein the transmitter repeatedly performs a transmission event of transmitting the ultrasound beam, and shifts the array of the transmission transducers in the azimuth direction for each of the transmission events, and the ultrasound signal processing device further comprises a synthesizer that generates a synthesized acoustic line signal by synthesizing a plurality of acoustic line signals by using positions of observation points as a reference, based on reflected ultrasound received from the subject in correspondence with each of the transmission events.

11. The ultrasound signal processing device of claim 10, wherein
in a range deeper than the focal point in the depth direction in the region of interest, the greater the number of acoustic line signals superposed with respect to the same observation point having the same position in the azimuth direction and the depth direction, the greater the number of the dependent observation points with respect to the reference observation point.

12. The ultrasound signal processing device of claim 1, wherein
when an array of transducers arranged along the azimuth direction is a first transducer array,
a plurality of second transducer arrays parallel to the first transducer array are arranged sandwiching the first transducer array, and
the delay-and-sum section, when generating acoustic line signals with respect to the same observation point having the same position in the azimuth direction and the depth direction,
(i) applies the reflected wave arrival times corresponding to the first transducer array to the second transducer arrays that are nearest to the first transducer array among the plurality of the second transducer arrays, and
(ii) applies reflected wave arrival times longer than the reflected wave arrival times corresponding to first transducer array to the second transducer arrays farther from the first transducer array than the second transducer arrays that are nearest to the first transducer array.

13. The ultrasound signal processing device of claim 1, wherein
when the reference observation point is a first reference observation point, the delay-and-sum section further selects a second reference observation point contiguous in the depth direction from the first reference observation point, calculates delay times of reflected wave arrival to each of the reception transducers from the second reference observation point as second reference delay times, and generates acoustic line signals by using the second reference delay times corresponding to the reception transducers, and
with respect to each of the one or more dependent observation points, calculates interpolated delay times by interpolation of the reference delay times and the second reference delay times based on a distance between the dependent observation point and the first reference observation point or the second reference observation point, and
with respect to each of the one or more dependent observation points, generates the acoustic line signals by applying the interpolated delay times corresponding to the reception transducers.

14. The ultrasound signal processing device of claim 1, wherein
the number of transducers included in the array of the transmission transducers increases as depth in the subject increases, in a range corresponding to a defined distance from a surface of the subject in the region of interest.

15. The ultrasound signal processing device of claim 1, wherein
in the generating of the acoustic line signals with respect to the one or more dependent observation points, the delay times of reflected wave arrival to each of the reception transducers from the one or more dependent observation points are not calculated.

16. The ultrasound signal processing device of claim 3, wherein
an ultrasound round-trip time between two points is a time obtained by dividing a round-trip distance between two points by a sound velocity value.

17. The ultrasound signal processing device of claim 1, wherein the delay-and-sum section includes an application number determiner that determines the number of dependent observation points PF to which the reference delay time of one reference observation point PR is applied based on a difference $\Delta d$ in path length between a reception transducer Rwk and adjacent ones of the observation points that are adjacent to each other in the depth direction.

18. An ultrasound signal processing method of transmitting an ultrasound beam into a subject by using an ultrasound probe in which transducers are arranged along an azimuth direction and generating acoustic line signals based on reflected waves obtained from the subject, the ultrasound signal processing method comprising:
causing an array of transmission transducers selected from the transducers to transmit the ultrasound beam;
based on reflected waves received by an array of reception transducers selected from the transducers, generating reception signal sequences corresponding to the reception transducers; and
for a reference observation point selected from observation points in a region of interest corresponding to an analysis target range of the subject, (i) calculating delay times of reflected wave arrival to each of the reception transducers from the reference observation point as reference delay times, and (ii) generating acoustic line signals by using the reference delay times corresponding to the reception transducers, and
for one or more dependent observation points in the region of interest that are contiguous in a depth direction from the reference observation point, (iii) generating acoustic line signals by applying the reference delay times corresponding to the reception transducers, wherein the delay times applied for the one or more dependent observation points are the same as the delay times applied for the reference observation point, and wherein the number of dependent observation points PF to which the reference delay time of one reference observation point PR is applied is minimum for a closest of the reference observation points to the array of reception transducers and is maximum for a furthest of the reference observation points from the array of reception transducers.

19. The ultrasound signal processing method of claim 18, wherein
the generating of the acoustic line signals with respect to the reference observation point is performed by calculating ultrasound round-trip time between the reference observation point and a reception transducer nearest to the reference observation point, calculating reflected wave arrival times that are each a sum of the ultrasound round-trip time and the reference delay time corresponding to the reception transducer, specifying reception signal values obtained from the reflected wave arrival times from reception signal sequences corresponding to the reception transducers, and performing summing with respect to the reception transducers, and
the generating of the acoustic line signals with respect to each of the one or more dependent observation points is performed by calculating ultrasound round-trip time between the dependent observation point and a reception transducer nearest to the dependent observation point, calculating approximate reflected wave arrival times that are each a sum of the ultrasound round-trip time and the reference delay time corresponding to the reception transducer, specifying reception signal values obtained from the approximate reflected wave arrival time from reception signal sequences corresponding to the reception transducers, and performing summing with respect to the reception transducers.

* * * * *